United States Patent
Yokota et al.

(10) Patent No.: US 9,833,586 B2
(45) Date of Patent: Dec. 5, 2017

(54) INTUBATION ASSISTANCE INSTRUMENT, INTUBATION ASSISTANCE APPARATUS AND INTUBATION ASSISTANCE SYSTEM

(75) Inventors: Hidetaka Yokota, Saitama (JP); Keizo Arakawa, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 1255 days.

(21) Appl. No.: 12/776,656

(22) Filed: May 10, 2010

(65) Prior Publication Data
US 2010/0288272 A1    Nov. 18, 2010

(30) Foreign Application Priority Data

May 18, 2009   (JP) ................. 2009-120253
May 18, 2009   (JP) ................. 2009-120254

(51) Int. Cl.
*A61M 16/00*   (2006.01)
*A61M 16/04*   (2006.01)
*A61B 1/267*   (2006.01)

(52) U.S. Cl.
CPC ......... *A61M 16/0488* (2013.01); *A61B 1/267* (2013.01)

(58) Field of Classification Search
USPC ............... 128/200.26, 207.14; 600/193–194; 24/648
See application file for complete search history.

(56) References Cited

U.S. PATENT DOCUMENTS

| | | | |
|---|---|---|---|
| 3,789,467 A * | 2/1974 | Aratani et al. .................. 24/648 |
| 5,174,283 A * | 12/1992 | Parker ..................... 128/200.26 |
| 5,261,392 A * | 11/1993 | Wu ................................ 600/188 |
| 6,471,643 B1 * | 10/2002 | Henderson ..................... 600/185 |
| 2006/0065268 A1 | 3/2006 | Koyama et al. |
| 2007/0106117 A1 | 5/2007 | Yokota |
| 2007/0106121 A1 | 5/2007 | Yokota et al. |

(Continued)

FOREIGN PATENT DOCUMENTS

| | | |
|---|---|---|
| JP | 2007-117114 | 5/2007 |
| JP | 2007-117115 | 5/2007 |

(Continued)

OTHER PUBLICATIONS

English translation of Japan Office Action in JP 2009-120253, dated Feb. 26, 2013.

(Continued)

*Primary Examiner* — Justine Yu
*Assistant Examiner* — Ned T Heffner
(74) *Attorney, Agent, or Firm* — Greenblum & Bernstein, P.L.C.

(57) ABSTRACT

An intubation assistance instrument includes: an elongated assistance instrument main body to be inserted into a target site of a patient from a mouth cavity or a nasal cavity of the patient; a guide member detachably attached to the assistance instrument main body, the guide member having a guide portion into which an intubation tube is to be inserted when the intubation tube is intubated into the target site of the patient, the guide portion capable of guiding the intubation tube to the target site; and a lock mechanism that locks the guide member to the assistance instrument main body when the guide member is attached to the assistance instrument main body.

20 Claims, 11 Drawing Sheets

(56) References Cited

U.S. PATENT DOCUMENTS

| | | |
|---|---|---|
| 2007/0106122 A1 | 5/2007 | Yokota et al. |
| 2007/0239137 A1 | 10/2007 | Stefanchik et al. |
| 2009/0143645 A1 | 6/2009 | Matthes |

FOREIGN PATENT DOCUMENTS

| | | |
|---|---|---|
| JP | 2007-268268 | 10/2007 |
| JP | 2007-301144 | 11/2007 |
| WO | 2009/051698 | 4/2009 |

OTHER PUBLICATIONS

English translation of Japan Office Action in JP 2009-120254, dated Feb. 26, 2013.

\* cited by examiner

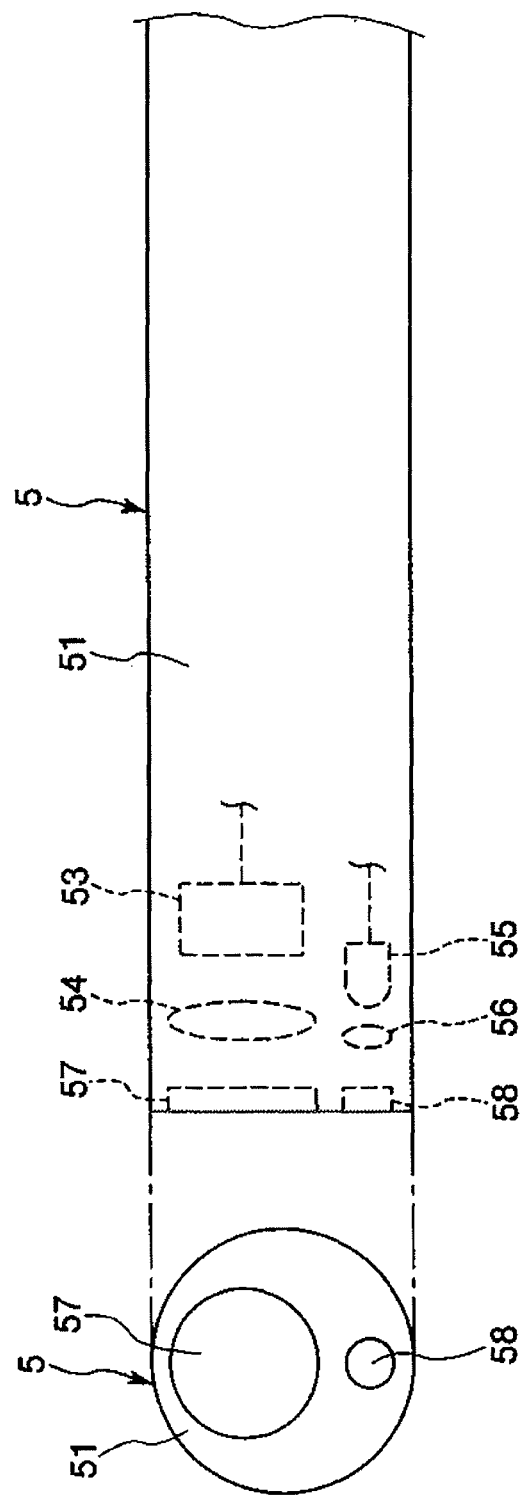

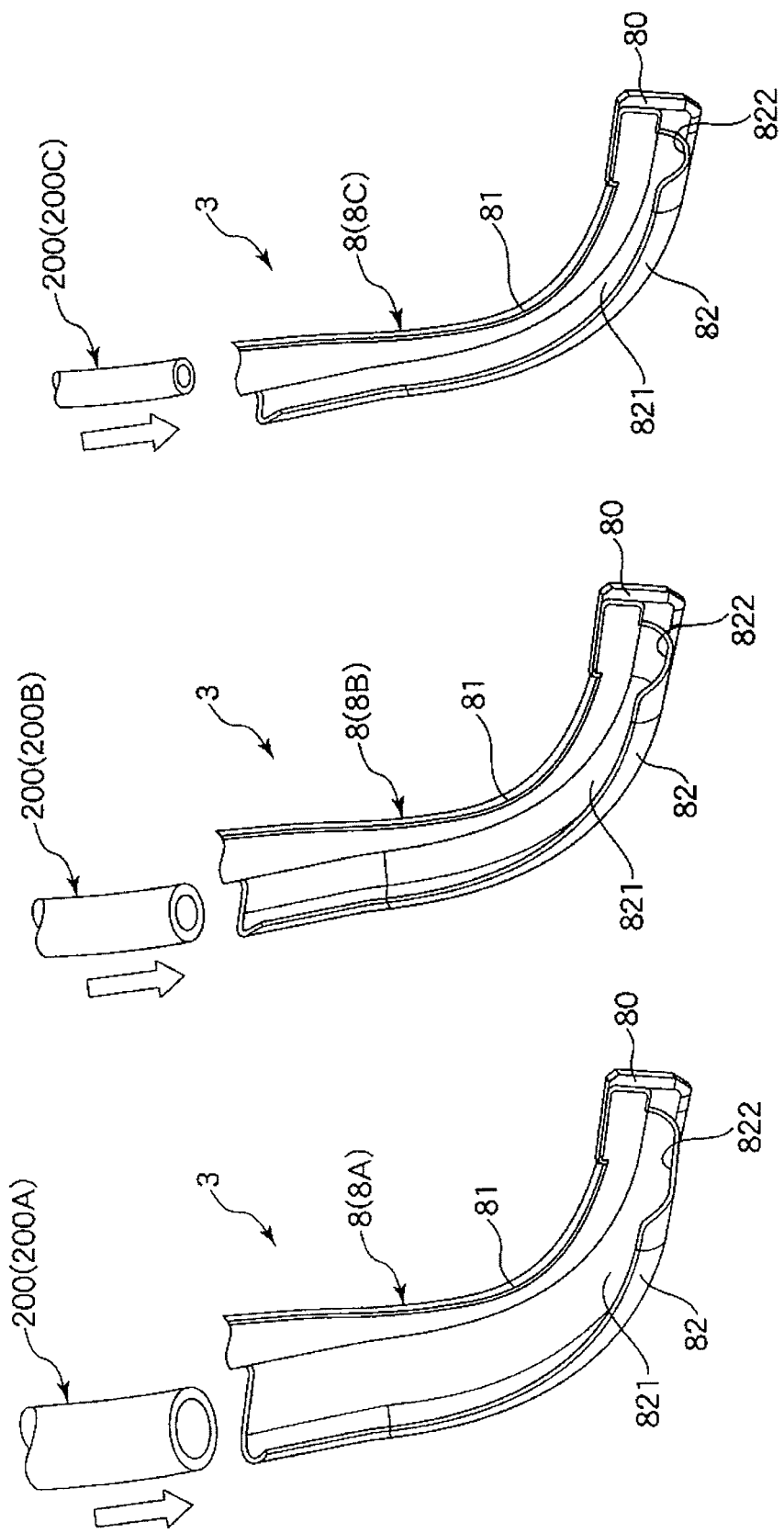

INTUBATION ASSISTANCE INSTRUMENT, INTUBATION ASSISTANCE APPARATUS AND INTUBATION ASSISTANCE SYSTEM

BACKGROUND OF THE INVENTION

Field of the Invention

The present invention relates to an intubation assistance instrument for use in intubating a distal end of an intubation tube into a target site such as a trachea of a patient, an intubation assistance apparatus including the intubation assistance instrument, and an intubation assistance system including the intubation assistance apparatus and an intubation tube.

Description of the Prior Art

It is sometimes necessary to practice artificial respiration, as a first-aid lifesaving treatment for a patient who is suffering from unconsciousness caused by an accident or the like. Although the artificial respiration may be practiced without using any instrument or apparatus, there is often a case that a respirator is used for that purpose.

In the case that a respirator is used to conduct artificial respiration, an intubation tube whose proximal end is connected to the respirator is inserted into a trachea of a patient to supply air to the trachea from the respirator via the tube.

In the meantime, if a patient loses consciousness, a root of a tongue is retracted to thereby block up a respiratory tract because of relaxation of muscles of a pharynx and a larynx and/or a gravity-caused loosening of a lower jaw.

Therefore, in the case where the afore-mentioned intubation tube is to be inserted into the trachea or a target site (such operation will be hereinafter referred to as "intubation operation"), it is essential to first open the blocked respiratory tract and secure an air passage by pulling up the tongue.

An intubation assistance apparatus to be used for securing the air passage is known (see, e.g., JP-A 2007-117115).

The intubation assistance apparatus described in JP-A 2007-117115 includes an apparatus main body, an intubation assistance instrument detachably mounted to the apparatus main body, and a laryngoscope for allowing an operator to observe the pharynx and the larynx, wherein the laryngoscope is configured so that it can be inserted into the intubation assistance instrument and removed therefrom.

The intubation assistance instrument is an elongated member with a curved middle portion and can be inserted through a mouth of a patient who has lost consciousness, for instance, whereby an appropriate portion on the side of the distal end comes into contact with and lifts up a tongue root portion of the patient, thus securing the air passage. Further, in the intubation assistance instrument, a groove in which an intubation tube can be inserted is formed along a longitudinal direction thereof.

For instance, after the intubation assistance apparatus described in JP-A 2007-117115 has been used, the intubation assistance instrument is detached from the intubation assistance apparatus and cleansed. In this case, there is a fear that the intubation assistance instrument cannot be sufficiently cleansed because it has a large size, a complex shape or the like.

Further, in the intubation assistance apparatus described in JP-A 2007-117115, since the intubation tube is repeatedly inserted into the groove and removed therefrom, the groove is easily abraded. Such an intubation assistance instrument having the abraded groove is not suitable for use in carrying out the intubation operation.

Therefore, even in the case where parts of the intubation assistance instrument other than the groove are normal (not damaged), the intubation assistance instrument has to be discarded. At that time, the normal parts are also discarded. This is wastefulness.

In addition, in such an intubation assistance apparatus, in the case where an operator wants to exchange a just inserted intubation tube to another intubation tube having a different outer diameter during the use of the intubation assistance apparatus, the operator has to mount another intubation assistance instrument corresponding to the other intubation tube to the apparatus main body after the intubation assistance instrument mounted to the apparatus main body has been removed therefrom.

Therefore, in such an intubation assistance apparatus, in the case where the operator wants to use an insertion tube having a different outer diameter, the operator has to exchange the entirety of the intubation assistance instrument. Further, in this case, the operator has to remove the laryngoscope from the intubation assistance instrument and insert it into the other intubation assistance instrument to be exchanged. This exchange operation is troublesome.

SUMMARY OF THE INVENTION

Accordingly, an object of the present invention is to provide an intubation assistance instrument, an intubation assistance apparatus and an intubation assistance system, each of which can be easily cleansed, in which only an easily abrading part can be appropriately discarded or exchanged.

Further, another object of the present invention is to provide an intubation assistance instrument, an intubation assistance apparatus and an intubation assistance system, each of which can selectively hold one of intubation tubes having different outer diameters when it is exchanged.

In order to achieve the object, the present invention includes the following features (1) to (15).

(1) An intubation assistance instrument, comprising: an elongated assistance instrument main body to be inserted into a target site of a patient from a mouth cavity or a nasal cavity of the patient; a guide member detachably attached to the assistance instrument main body, the guide member having a guide portion into which an intubation tube is to be inserted when the intubation tube is intubated into the target site of the patient, the guide portion capable of guiding the intubation tube to the target site; and a lock mechanism that locks the guide member to the assistance instrument main body when the guide member is attached to the assistance instrument main body.

This makes it possible to easily cleanse the intubation assistance instrument, and to appropriately discard or exchange only an easily abrading part of the intubation assistance instrument.

(2) The intubation assistance instrument according to the above feature (1), wherein the intubation assistance instrument is configured to selectively intubate one of intubation tubes having different outer diameters, wherein the intubation assistance instrument comprises, as the guide member, a plurality of guide members each having a guide portion with a shape and a size corresponding to the outer diameter of the intubation tube to be inserted into the guide portion, and wherein one of the plurality of guide members is selected depending on the intubation tube to be intubated into the target site, and the selected guide member is detachably attached to the assistance instrument main body.

This makes it possible to promptly exchange the intubation tubes having the different outer diameters.

(3) The intubation assistance instrument according to the above feature (1), wherein the lock mechanism includes: a pair of engagement portions provided in a mutually facing relationship so as to come close to and separate from each other, the engagement portions capable of engaging with the guide member; a bias portion that biases the engagement portions so that they come close to each other; and operation portions that are operated for unlocking the engagement between the engagement portions and the guide member against biasing force of the bias portion.

This makes it possible to easily attach the guide member to and detach it from the assistance instrument main body.

(4) The intubation assistance instrument according to the above feature (3), wherein each of the engagement portions is rotatably attached to the assistance instrument main body.

This makes it possible to easily attach the guide member to and detach it from the assistance instrument main body.

(5) The intubation assistance instrument according to the above feature (3), wherein each of the engagement portions has an inclined portion inclining with respect to an attaching direction of the guide member to the assistance instrument main body.

This makes it possible to easily carry out an attaching operation of the guide member to the assistance instrument main body.

(6) The intubation assistance instrument according to the above feature (1), wherein the guide member is attached to and detached from the assistance instrument main body by moving the guide member along a longitudinal direction of the assistance instrument main body, and wherein the intubation assistance instrument further comprises a restriction means that restricts a moving direction of the guide member.

This makes it possible to easily carry out an attaching and detaching operation of the guide member to the assistance instrument main body.

Further, for example, the restriction means can be configured so that the moving direction of the guide member is restricted to a direction toward a proximal end portion of the assistance instrument main body when the guide member is attached to the assistance instrument main body and is restricted to a direction toward a distal end portion of the assistance instrument main body when the guide member is detached from the assistance instrument main body. In this case, the attaching and detaching operation can be carried out at the side of the distal end portion of the assistance instrument main body.

Therefore, even if an apparatus main body of an intubation assistance apparatus is mounted to the proximal end portion of the assistance instrument main body, since the attaching and detaching operation is carried out at the side of the distal end portion of the assistance instrument main body, that is, at the side opposite to the apparatus main body, it is possible to prevent the apparatus main body from disturbing the attaching and detaching operation. This makes it possible to more easily carry out such an attaching and detaching operation.

(7) The intubation assistance instrument according to the above feature (6), wherein the restriction means is composed of a groove provided on one of the assistance instrument main body and the guide member and a protruding portion inserted into the groove and provided on the other.

This makes it possible to make the restriction means into a simple structure. Therefore, the attaching and detaching operation of the guide member to the assistance instrument main body can be more easily carried out using the restriction means having such a simple structure.

(8) The intubation assistance instrument according to the above feature (1), wherein the guide member has an elongated shape, and the guide portion is composed of a recess formed so as to extend along a longitudinal direction of the guide member.

This makes it possible to easily carry out an intubation operation of intubating the intubation tube into a trachea or the like.

(9) The intubation assistance instrument according to the above feature (8), wherein an inner surface of the recess is subjected to a treatment of reducing friction between the intubation tube and the inner surface of the recess.

This makes it possible to easily carry out an intubation operation of intubating the intubation tube into a trachea or the like.

(10) The intubation assistance instrument according to the above feature (8), wherein the assistance instrument main body has a tube restriction portion that prevents the intubation tube inserted into the recess from being removed therefrom.

This makes it possible to prevent the intubation tube inserted into the recess from being removed therefrom during a course of an intubation operation of intubating the intubation tube into a trachea or the like.

(11) The intubation assistance instrument according to the above feature (1), wherein the assistance instrument main body has a plate-like protruding portion provided on a distal end portion of the assistance instrument main body so as to protrude in a frontward direction.

This makes it possible to lift up an epiglottis of a patient with the protruding portion during a course of an intubation operation of intubating the intubation tube into a trachea or the like to thereby secure an air passage for the patient in an easy and reliable manner.

(12) The intubation assistance instrument according to the above feature (11), wherein the assistance instrument main body includes a curved portion formed at a roughly middle part thereof, the curved portion having a curved inner side, and wherein the protruding portion is formed so as to continuously extend from the curved inner side at the distal end portion of the assistance instrument main body.

This makes it possible to lift up an epiglottis of a patient with the protruding portion during a course of an intubation operation of intubating the intubation tube into a trachea or the like to thereby secure an air passage for the patient in an easy and reliable manner.

(13) An intubation assistance apparatus, comprising: the intubation assistance instrument according to the above feature (1); an apparatus main body to which the assistance instrument main body of the intubation assistance instrument is mounted; and an image light acquiring means that acquires image light of an observation site at which a distal end portion of the intubation assistance instrument is positioned.

This makes it possible to easily cleanse the intubation assistance instrument, and to appropriately discard or exchange only an easily abrading part of the intubation assistance instrument.

(14) The intubation assistance apparatus according to the above feature (13), wherein the guide member can be attached to and detached from the assistance instrument main body in a state that the assistance instrument main body is mounted to the apparatus main body.

This makes it possible to prevent the apparatus main body from disturbing an attaching and detaching operation of the guide member. Therefore, it is possible to easily and promptly carry out such an attaching and detaching operation.

(15) An intubation assistance system, comprising: the intubation assistance apparatus according to the above feature (13); and an insertion tube to be inserted into the guide portion of the guide member of the intubation assistance instrument.

This makes it possible to easily cleanse the intubation assistance instrument, and to appropriately discard or exchange only an easily abrading part of the intubation assistance instrument.

Effect of the Present Invention

According to the present invention, by a simple operation which is an operation of acting on the lock mechanism, the guide member can be easily attached to and detached from the assistance instrument main body. Therefore, the detached guide member and the assistance instrument main body from which the guide member has been detached can be separately cleansed, to thereby sufficiently clean them.

Further, the guide member is abraded by repeatedly inserting an intubation tube thereinto and removing the intubation tube therefrom. For example, in the case where the guide member is abraded, the abraded guide member is exchanged to a new guide member, and then the new guide member can be attached to the assistance instrument main body.

Therefore, according to the present invention, a single assistance instrument main body can be shared by the guide members and the guide members can be consumables. The assistance instrument main body can be used for a long period of time only by exchanging the consumables (guide members). For this reason, the present invention can eliminate waste losses.

In addition, in the case where the intubation assistance instrument is configured so that detachably attached to the assistance instrument main body are the guide members prepared corresponding to outer diameters of the intubation tubes, an operator can select one of the guide members corresponding to an intubation tube to be used, and then attach the selected guide member to the assistance instrument main body. This makes it possible to promptly exchange the intubation tubes having different outer diameters.

BRIEF DESCRIPTION OF THE DRAWINGS

FIG. 10A is a front view showing a laryngoscope included in the intubation assistance apparatus according to the present invention, and FIG. 10B is a side view showing the laryngoscope.

FIGS. 11A to 11C are perspective views illustrating guide members of three types each included in the intubation assistance instrument shown in FIG. 1.

DETAILED DESCRIPTION OF THE PREFERRED EMBODIMENT

Hereinbelow, preferred embodiments of an intubation assistance instrument, an intubation assistance apparatus and an intubation assistance system according to the present invention will be described in detail with reference to the accompanying drawings.

Figure 1:
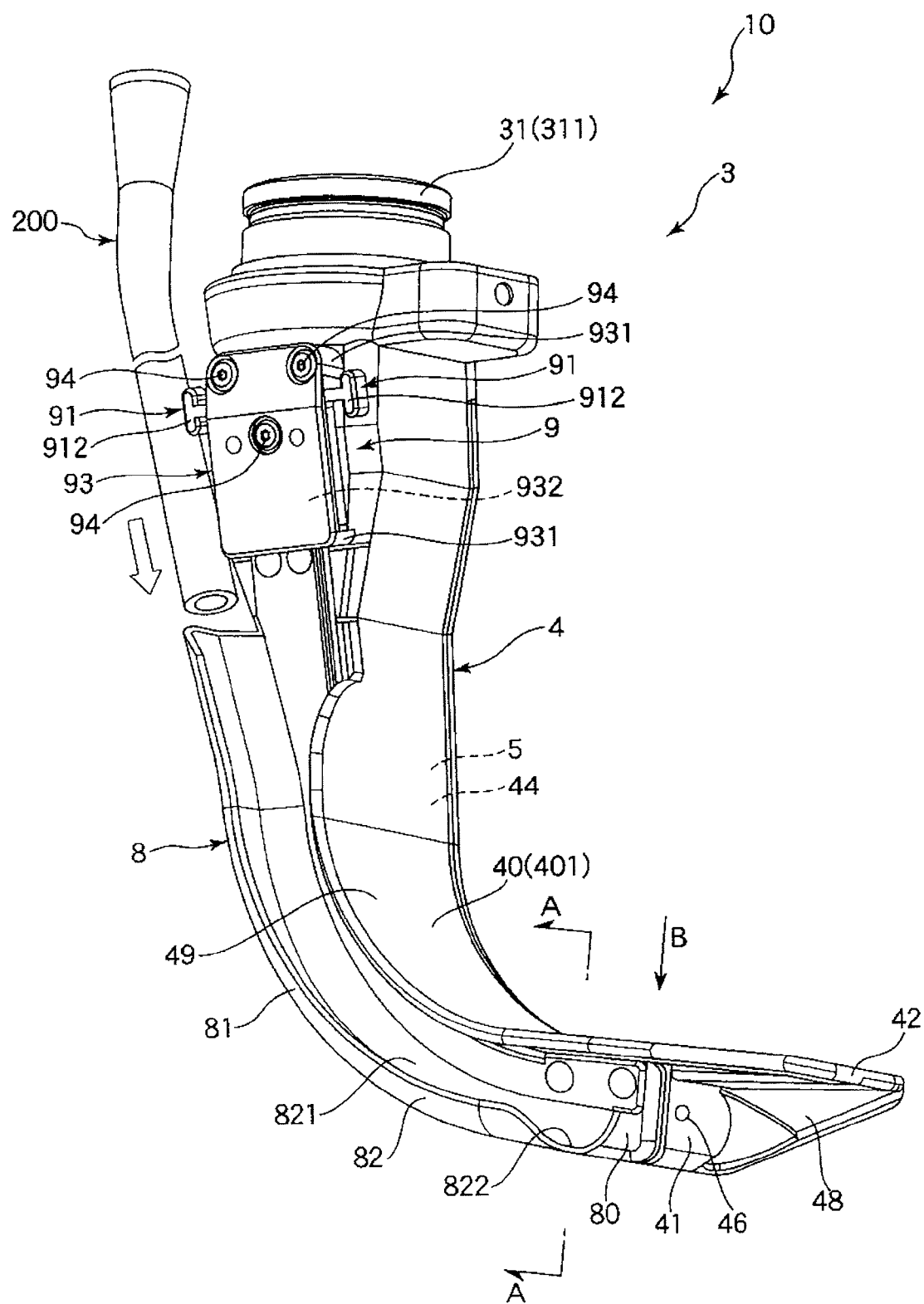
FIG. 1 is a perspective view showing an embodiment of an intubation assistance instrument (intubation assistance system) according to the present invention.
Figure 2:
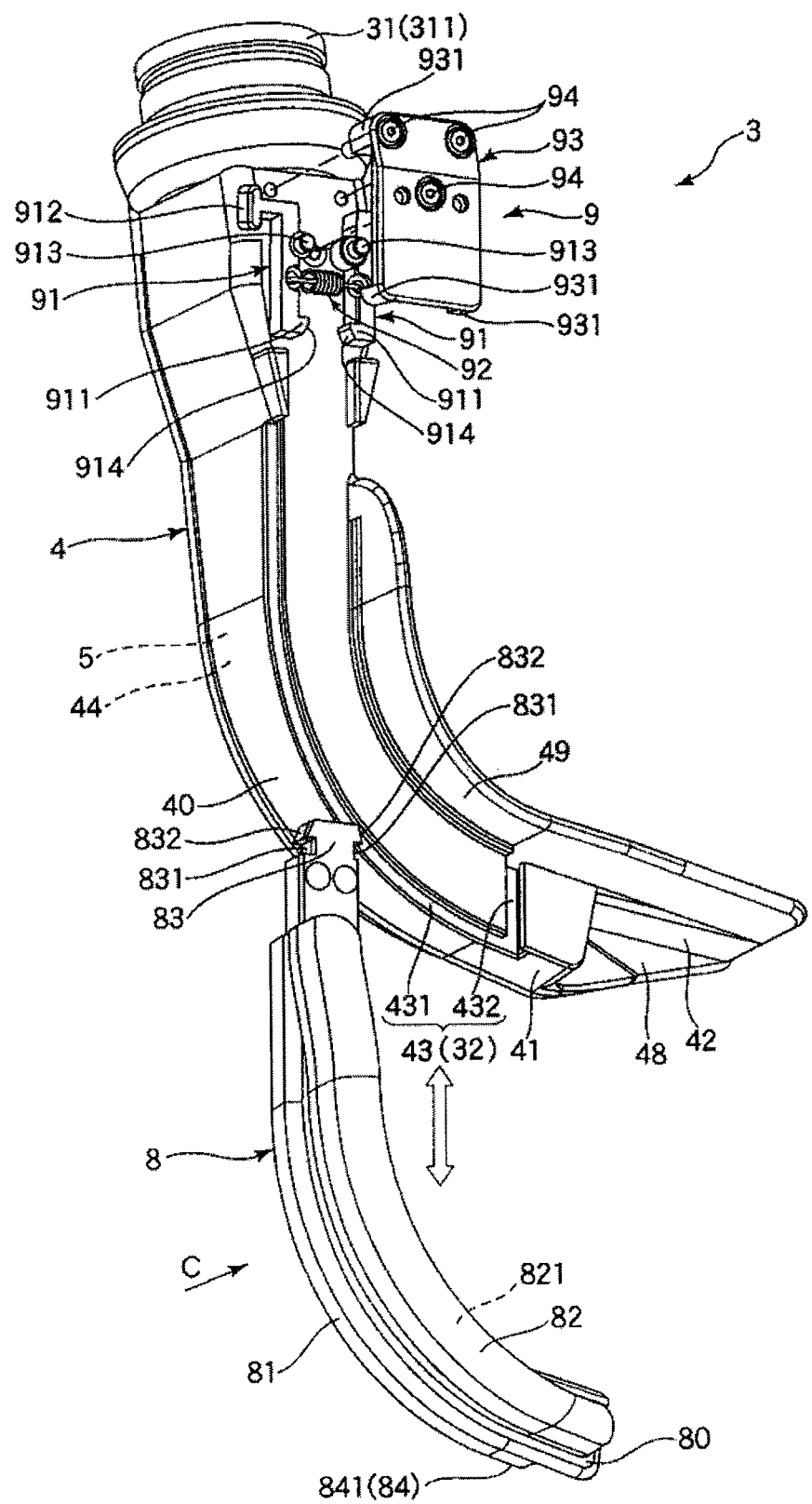
FIG. 2 is an exploded perspective view illustrating the intubation assistance instrument shown in FIG. 1.
Figure 3:
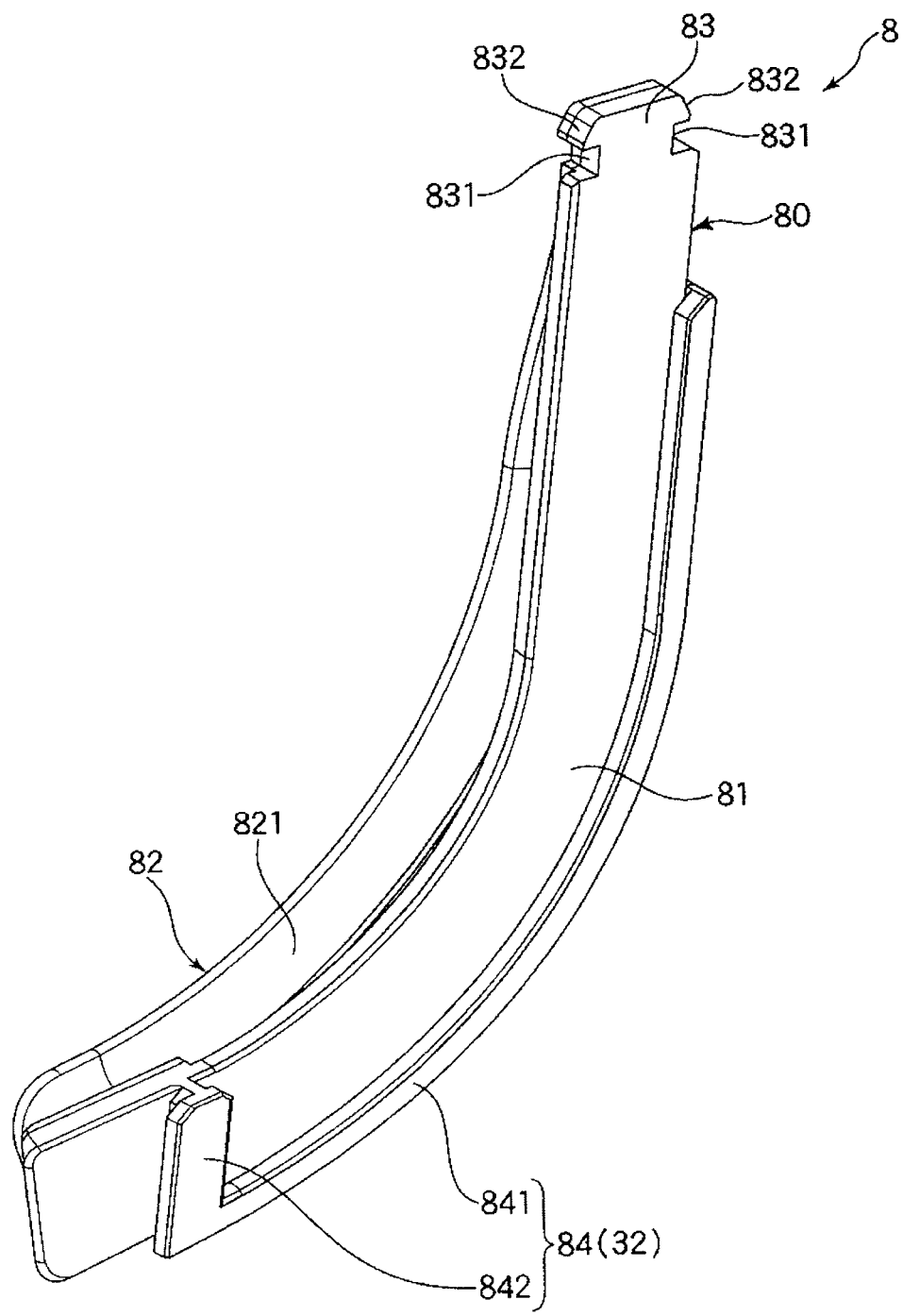
FIG. 3 is a view illustrating a guide member shown in FIG. 2 when viewed from the side of the arrow C.

FIG. 1 is a perspective view showing an embodiment of the intubation assistance instrument (intubation assistance system) according to the present invention, FIG. 2 is an exploded perspective view illustrating the intubation assistance instrument shown in FIG. 1, and FIG. 3 is a view illustrating a guide member shown in FIG. 2 when viewed from the side of the arrow C.

Figure 4:
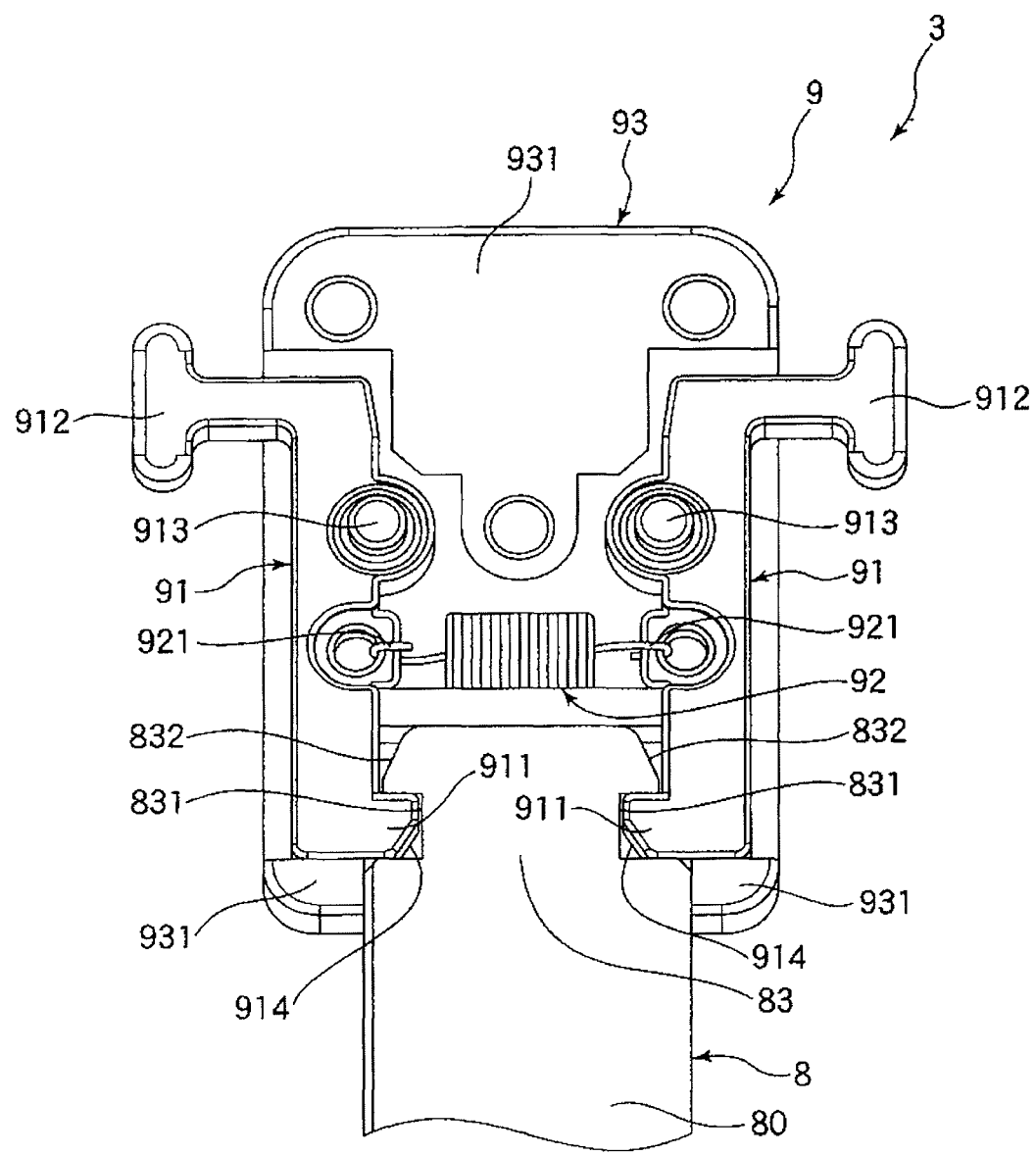
FIG. 4 is a rearview (in a state that a guide member is attached to an assistance instrument main body) showing a lock mechanism included in the intubation assistance instrument shown in FIG. 1 when viewed from the side of a rear surface of a cover of the lock mechanism.
Figure 5:
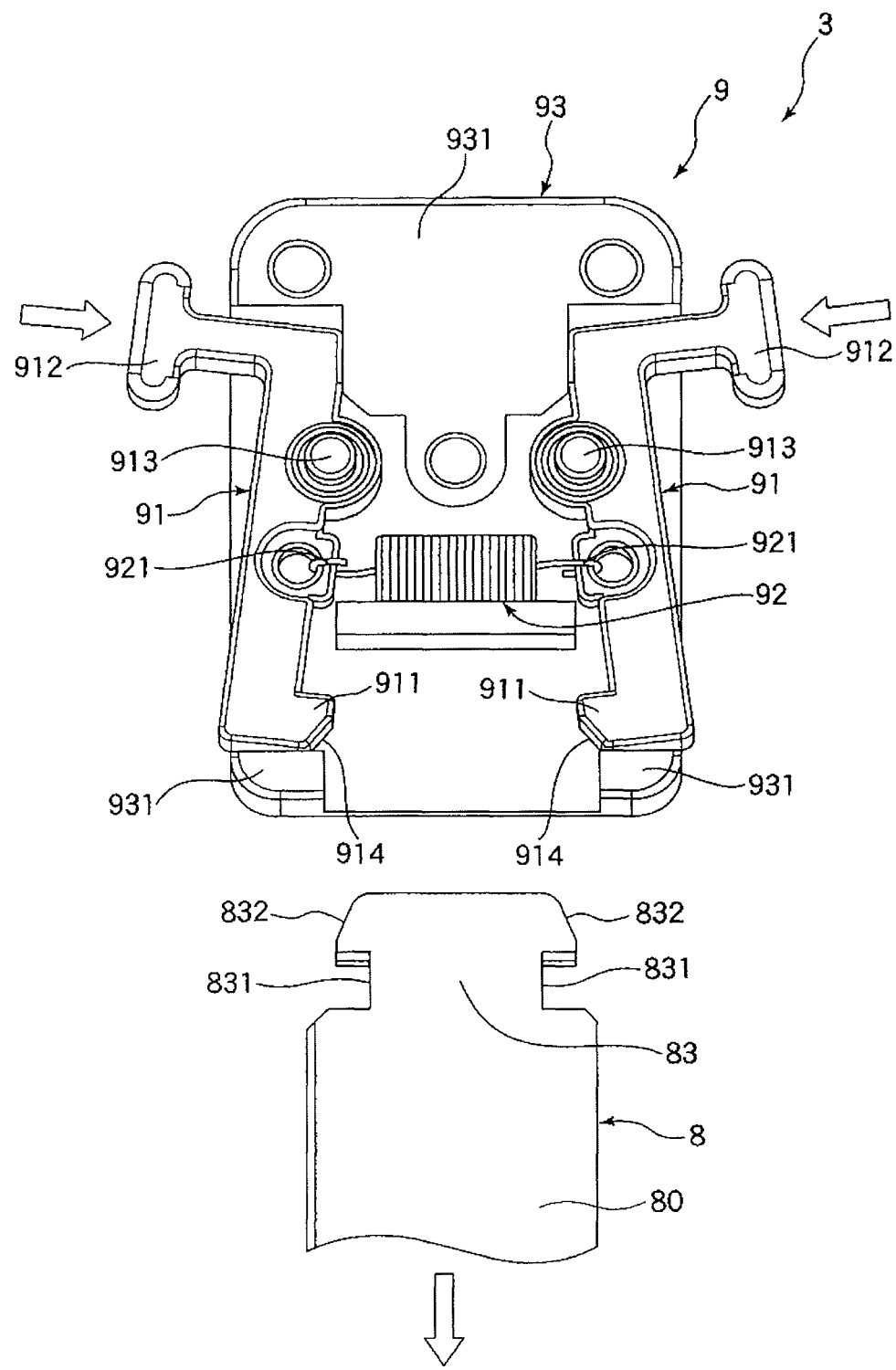
FIG. 5 is a rear view (in a state that the guide member is detached from the assistance instrument main body) showing the lock mechanism included in the intubation assistance instrument shown in FIG. 1 when viewed from the side of the rear surface of the cover of the lock mechanism.

FIG. 4 is a rearview (in a state that a guide member is attached to an assistance instrument main body) showing a lock mechanism included in the intubation assistance instrument shown in FIG. 1 when viewed from the side of a rear surface of a cover of the lock mechanism, and FIG. 5 is a rear view (in a state that the guide member is detached from the assistance instrument main body) showing the lock mechanism included in the intubation assistance instrument shown in FIG. 1 when viewed from the side of the rear surface of the cover of the lock mechanism.

Figure 6:
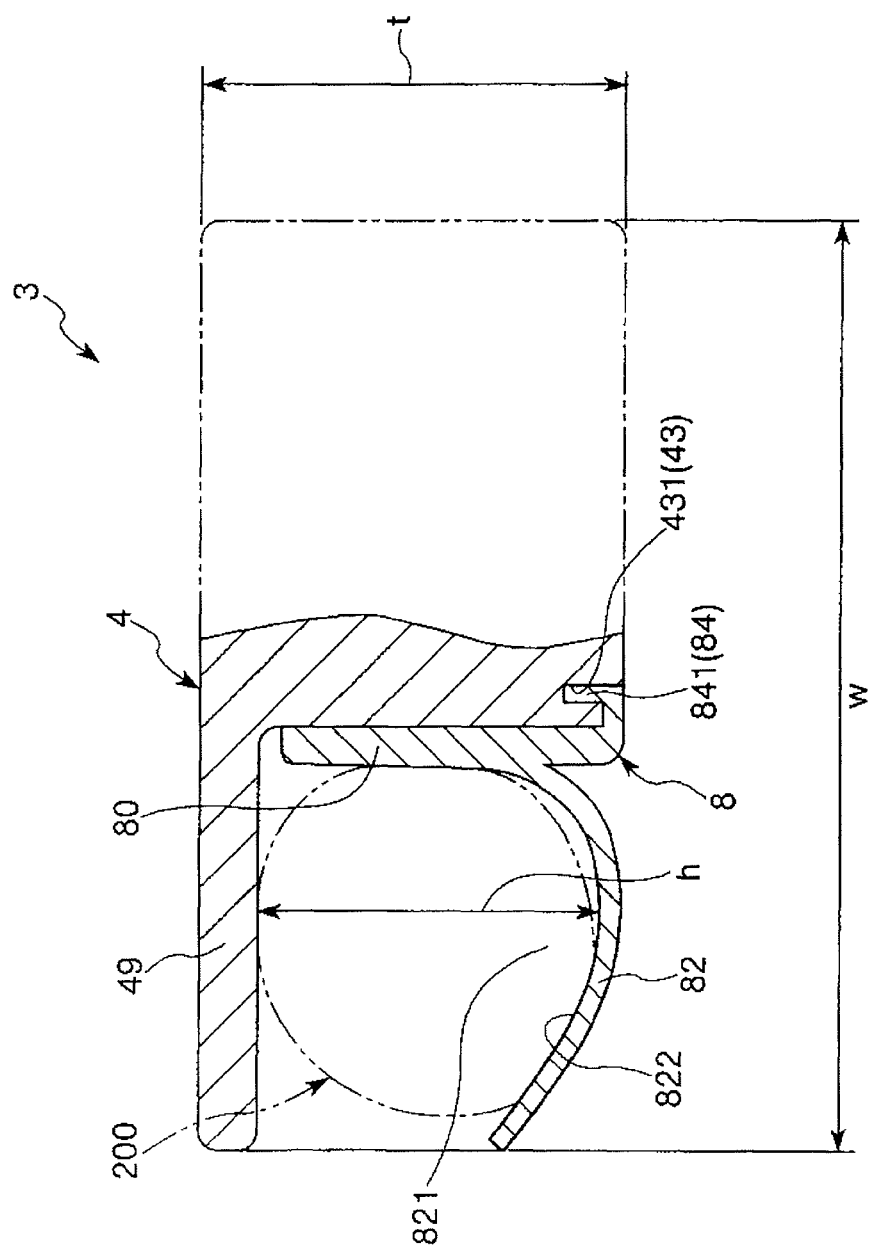
FIG. 6 is a cross-sectional view illustrating the intubation assistance instrument cut along the A-A line shown in FIG. 1.
Figure 7:
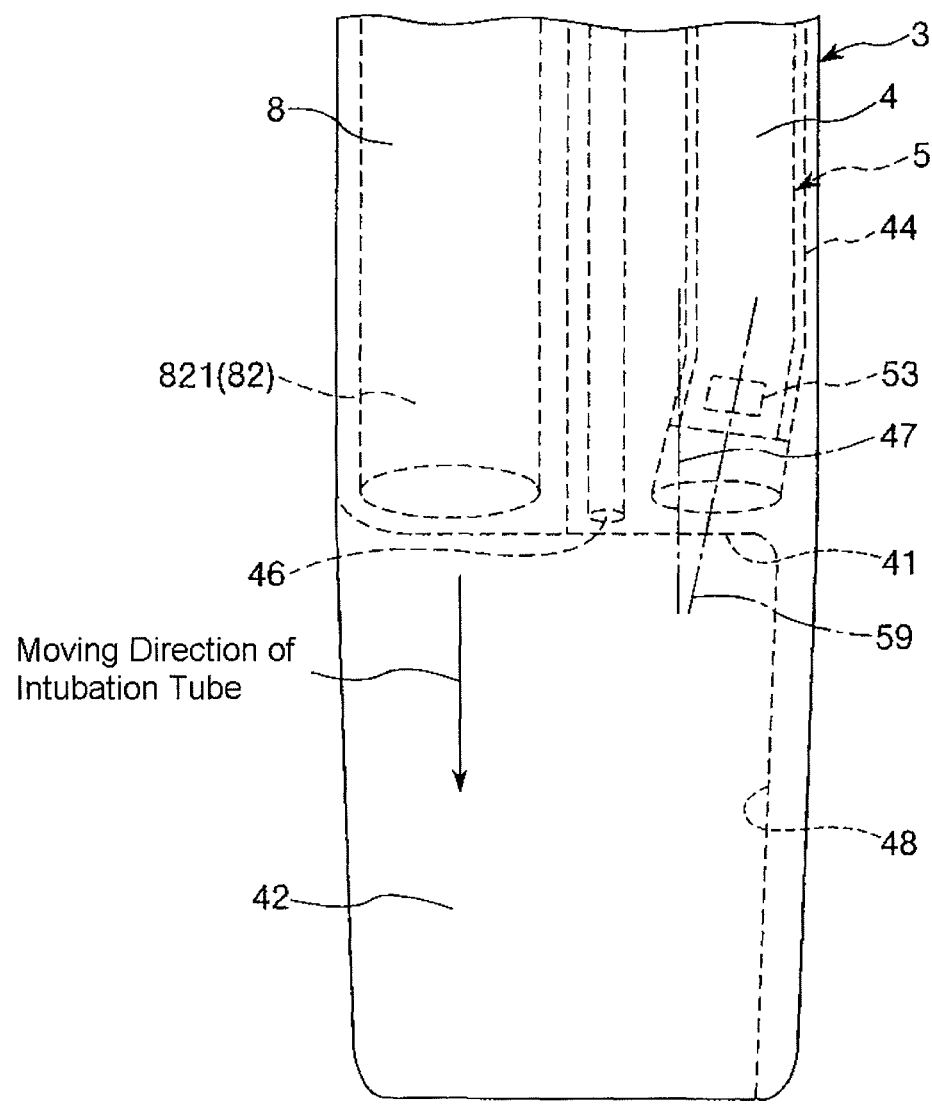
FIG. 7 is a view illustrating the intubation assistance instrument shown in FIG. 1 when viewed from the side of the arrow B.
Figure 8:
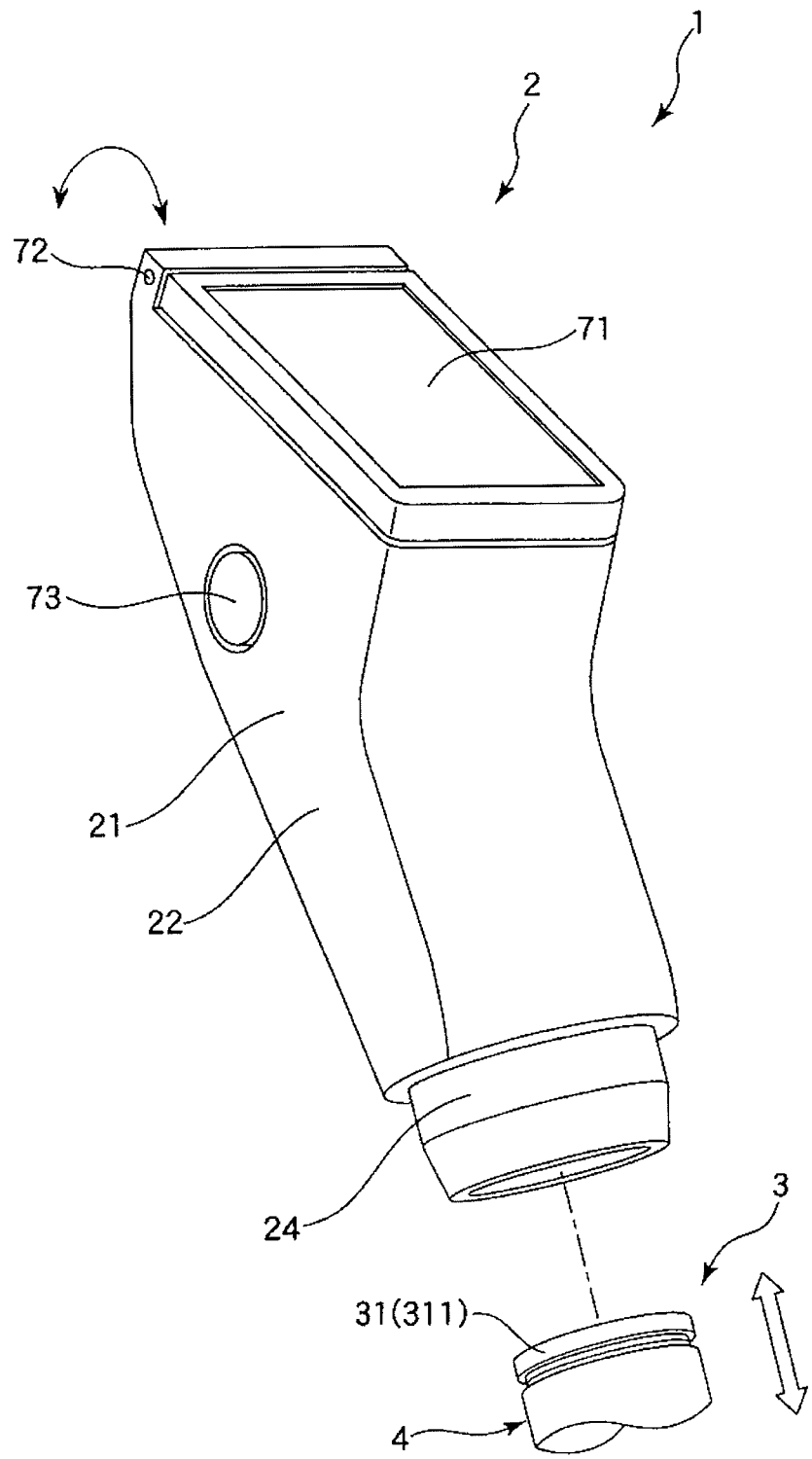
FIG. 8 is a perspective view showing an apparatus main body included in an intubation assistance apparatus according to the present invention.

FIG. 6 is a cross-sectional view illustrating the intubation assistance instrument cut along the A-A line shown in FIG. 1, FIG. 7 is a view illustrating the intubation assistance instrument shown in FIG. 1 when viewed from the side of the arrow B, and FIG. 8 is a perspective view showing an apparatus main body included in an intubation assistance apparatus according to the present invention.

Figure 9:
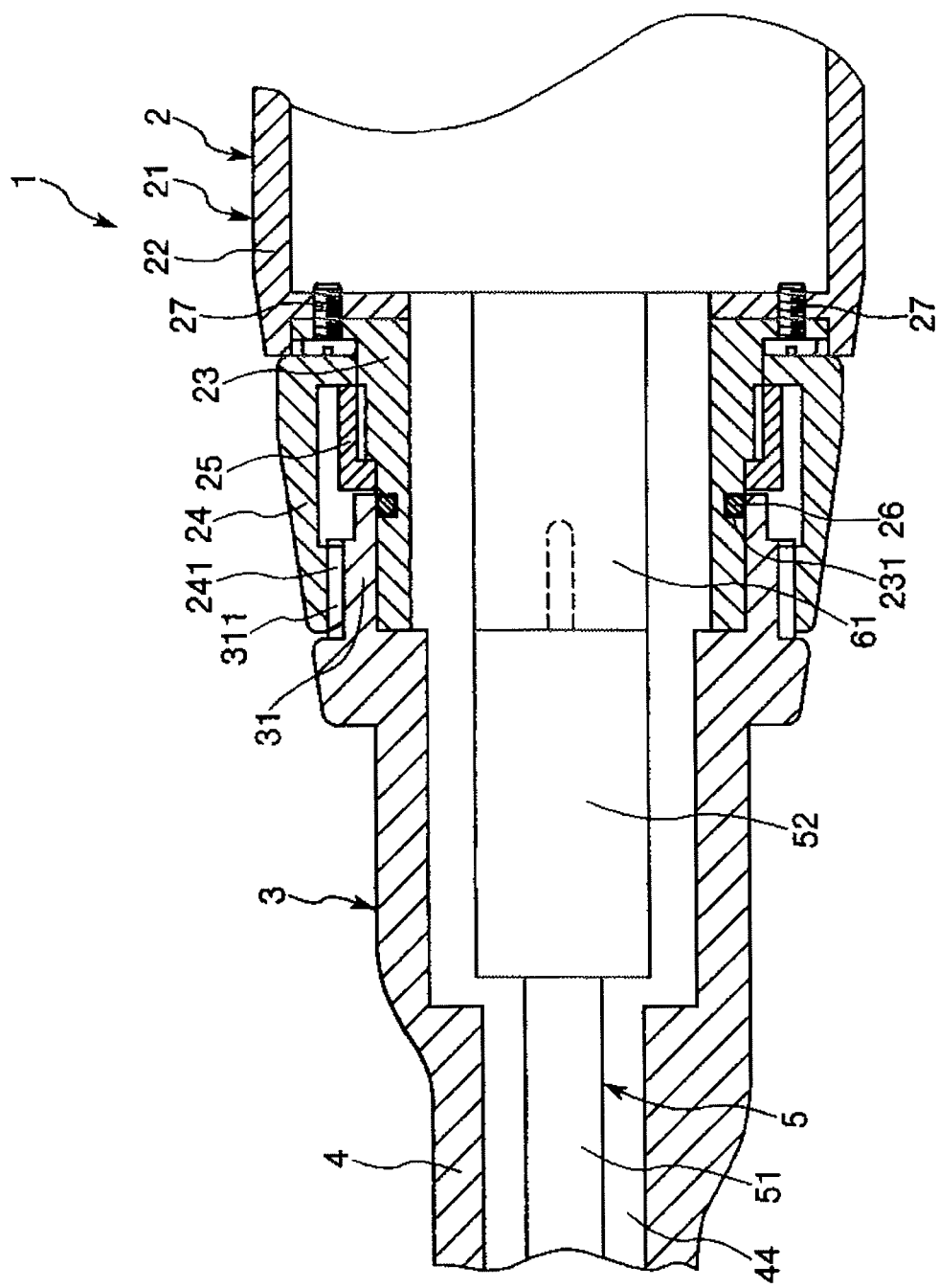
FIG. 9 is a cross-sectional view showing a connection portion (coupling portion) of the apparatus main body and the intubation assistance instrument of the intubation assistance apparatus according to the present invention.

FIG. 9 is a cross-sectional view showing a connection portion (coupling portion) of the apparatus main body and the intubation assistance instrument of the intubation assistance apparatus according to the present invention, FIG. 10A is a front view showing a laryngoscope included in the intubation assistance apparatus according to the present invention, and FIG. 10B is a side view showing the laryngoscope.

In the following description, the lower side and the upper side in FIGS. 1 to 5, 7 and 8 will be referred to as "distal end" and "proximal end", respectively, for the purpose of clarity. However, it should be noted that a direction of the distal end varies in the drawings because the intubation assistance instrument is curved in its midway portion. The left side and the right side in FIGS. 9, 10A and 10B will be referred to as "distal end" and "proximal end", respectively.

The intubation assistance apparatus 1 shown in these drawings includes an apparatus main body 2, an intubation assistance instrument 3 detachably mounted to the apparatus main body 2 and a laryngoscope 5 to be inserted into the intubation assistance instrument 3.

As will be described later, the intubation assistance apparatus 1 is used in combination with an intubation tube 200 which is to be inserted into a trachea of a patient through the mouth (mouth cavity) thereof (see, FIG. 1). An intubation assistance system 10 comprised of a combination of the intubation assistance apparatus 1 and the intubation tube 200 (see, FIG. 1).

As shown in FIG. 1, the intubation tube 200 has a substantially circular cross-section and is formed of a flexible or pliable material such as elastomer, rubber, and the like.

As shown in FIG. 8, the apparatus main body 2 is provided with a casing 21 and has a water-proof structure which may be, for example, one of conventional water-proof structures (configurations) known in the art.

Referring to FIG. 9, the casing 21 includes a case body 22 and an annular coupling portion 23 provided on a distal end side of the case body 22. The case body 22 and the annular coupling portion 23 are fastened to each other by means of bolts (screws) 27.

In this case, a gap between the case body 21 and the annular coupling portion 23 is fluid-tightly (air-tightly) sealed with a sealing member (sealing means), e.g. a packing, not shown in the drawings. Alternatively, the case body 21 and the annular coupling portion 23 may be integrally formed with each other.

An annular operating sleeve 24 is provided on an outer circumference of the coupling portion 23 for forward and reverse rotation (in a rotatable manner). Separation of the operating sleeve 24 from the coupling portion 23 is inhibited by means of a retainer member 25. A female thread 241 is formed on an inner circumference of a distal end portion of the operating sleeve 24.

On the other hand, on an outer circumference of a proximal end portion 31 of the intubation assistance instrument 3 (assistance instrument main body 4), there is formed a male thread 311 that threadedly engages with the female thread 241 of the operating sleeve 24.

Further, a groove 231 is formed on the outer circumference of the coupling portion 23 and a sealing member (sealing means) 26 such as a packing is fitted into the groove 231.

In order to mount or affix the intubation assistance instrument 3 to the apparatus main body 2, a proximal end portion 31 of the intubation assistance instrument 3 is inserted between the coupling portion 23 of the casing 21 of the apparatus main body 2 and the operating sleeve 24, after which the operating sleeve 24 is rotated in a predetermined direction.

This enables the intubation assistance instrument 3 to displace in a proximal end direction with respect to the apparatus main body 2, whereby the intubation assistance instrument 3 is mounted (attached) to the apparatus main body 2.

Under the state that the intubation assistance instrument 3 has been mounted to the apparatus main body 2, a gap between the coupling portion 23 of the apparatus main body 2 and the proximal end portion 31 of the intubation assistance instrument 3 is fluid-tightly (air-tightly) sealed by means of the sealing member 26.

This provides fluid-tight (air-tight) sealing to a proximal end side of a scope guide bore 44 of the assistance instrument main body 4 of the intubation assistance instrument 3 which will be described below. Thus, the scope guide bore 44 is fluid-tightly (air-tightly) sealed up in its entirety, whereby making it possible to reliably prevent any contamination of the laryngoscope 5 disposed within the scope guide bore 44.

In order to remove the intubation assistance instrument 3 from the apparatus main body 2, the operating sleeve 24 is rotated in a direction opposite to the direction described above. This causes the intubation assistance instrument 3 to displace in a distal end direction with respect to the apparatus main body 2, whereby the female thread 241 is disengaged from the male thread 311, eventually allowing the intubation assistance instrument 3 to be removed from the apparatus main body 2.

A method of mounting or affixing the intubation assistance instrument 3 to the apparatus main body 2, i.e., a method of connecting or coupling the intubation assistance instrument 3 and the apparatus main body 2 together, is not restricted to the afore-mentioned one (thread coupling method), but may include a variety of other alternative methods, e.g., a ratchet mechanism method, a bayonet mounting method, a cam method, a locking claw method and a magnetic method.

Referring to FIG. 8, a display (image displaying means) 71 is mounted on a proximal end portion of the apparatus main body 2 so as to be rotatable (displaceable) about a shaft 72. In this case, the display 71 may be designed to be manually rotated by an operator or automatically rotated by driving power of a drive power source such as an electric motor.

The display 71 is comprised of, e.g., a liquid crystal display device, an organic EL display device or the like and serves to display an image corresponding to an image light acquired by an image light acquiring means, namely, an image (electronic image) of an observation site taken by a CCD 53.

The display 71 is adapted to display a target mark for specifying a location of a rima glottides to easily insert a distal end portion of the intubation tube 200 into a trachea from the rima glottidis, an indicator sign for showing a remaining battery level of a power source described later, a battery warning mark for informing an operator of a battery exchange time when the battery is used up, a lapse time (intubation operation time) counted from beginning of an intubation operation, which is to avoid a situation that a patient is in an apnea condition for an extended period of time due to a difficulty encountered in the intubation operation, and so forth.

Owing to the fact that the display 71 is rotatable with respect to the apparatus main body 2, the display 71 can be oriented in any desired direction regardless of a direction in which the intubation assistance instrument 3 extends. Accordingly, the image displayed on the display 71 can be readily seen regardless of a posture of a patient or a position of an operator, thus enabling the operator to carry out the intubation operation in an easy and reliable manner.

Furthermore, the display 71 may be configured such that it can be detachably mounted to the apparatus main body 2.

A detection means may be additionally provided for detecting the rotation angle (rotation amount) of the display 71 with respect to the main body 2, and the image displayed on the display 71 may be inverted depending on the result of detection.

In addition, the display 71 may be designed to rotate not only in the single axis direction noted above but also in two-axes or three-axes directions, for instance.

As shown in FIG. 9, a connector portion 61 connected to a connector portion 52 of the laryngoscope 5 is provided in a position inside the apparatus main body 2 corresponding to the coupling portion 23. Also provided within the apparatus main body 2 are a circuit board connected to the connector portion 61 and the display 71 and a power source and an input/output part connected to the circuit board, which components are not shown in the drawings.

The circuit board includes a LED driving circuit (illuminator driving circuit) for driving the white LED 55, a CCD driving circuit (image pickup device driving circuit) for driving the CCD 53, an image processing circuit for processing the image data outputted from the CCD 53, an image display circuit for converting the image data outputted from the image processing circuit to image data for use in the display 71 and causing an image to be displayed on the display 71, a storage part (storage means) for storing the image data, a central processing circuit and the like.

A battery is removably attached to the power source from which electric power is supplied to various parts including the circuit board.

The input/output part includes an external power input terminal through which external power is inputted or supplied, an external monitor output terminal through which the image data is outputted to an external monitor, and an image storing memory terminal to which a memory card (removable memory device) such as a SD card or a CF card is connected.

As illustrated in FIG. 8, a cover 73 is attached to a left side surface of the casing 21 of the apparatus main body 2. The cover 73 is opened to gain access to the respective one of the external power input terminal, the external monitor output terminal and the image storing memory terminal.

In order to avoid any inadvertent opening or closing, the cover 73 is designed such that it can be opened or closed only with the use of a special tool. A gap between the cover 73 and the casing 21 is fluid-tightly (air-tightly) sealed by means of a sealing member (sealing means) such as a packing not shown in the drawings.

As illustrated in FIG. 9, a laryngoscope 5 is connected to the apparatus main body 2. This laryngoscope 5 is disposed or received inside a scope guide bore (internal bore) 44 so as to be removable therefrom. In this regard, it is to be noted that the scope guide bore 44 serves as a disposing portion on which at least a part of the laryngoscope 5 (the entirety in this embodiment) is disposed.

Such a scope guide bore 44 is formed inside the assistance instrument main body 4 so as to extend from the proximal end portion to a distal end wall 41, namely, along a longitudinal direction of the assistance instrument main body 4. In the case where the laryngoscope 5 is disposed inside the scope guide bore 44, a distal end portion of the laryngoscope 5 is arranged at a distal end portion of the scope guide bore 44 (see, FIG. 8).

The laryngoscope 5 is a device (means) that functions as both an image light acquiring means for acquiring image light of an observation site (an image taking means for taking an image of an object) in front of the distal end wall 41 of the assistance instrument main body 4 and an illumination means for illuminating the observation site.

As shown in FIGS. 9 and 10, the laryngoscope 5 includes a flexible elongated body portion 51 and a connector portion 52 provided on a proximal end portion of the body portion 51. By virtue of the connector portion 52, the laryngoscope 5 is detachably and mechanically connected to a connector portion 61 of the apparatus main body 2 set forth below. As a consequence, the laryngoscope 5 and the apparatus main body 2 are electrically connected with each other.

As shown in FIG. 10, a CCD (image pickup device) 53 and a white LED (light emitting diode) 55 serving as a light source are provided within a distal end portion of the body portion 51. One or more image taking lenses (a set of lenses) including an objective lens 54 are provided at a distal end portion of the CCD 53 of the body portion 51, whereas an illumination lens 56 is arranged at a distal end portion of the white LED 55. In the following, the image taking lens including the objective lens 54 will be simply referred to as "objective lens 54".

More specifically, two holes opened at their tip ends (not shown in the drawings) are formed on the distal end portion of the body portion 51. The CCD 53 and the objective lens 54 are arranged within one of the holes, a tip end of which is fluid-tightly sealed by means of a window portion 57 having optical transparency.

The white LED 55 and the illumination lens 56 are arranged within the other of the holes, a tip end of which is fluid-tightly sealed by means of a window portion 58 having optical transparency. As an alternative, the illumination lens 56 may be omitted and the window portion 58 may play a role of the illumination lens 56.

By arranging the CCD 53 and the objective lens 54 in one hole and the white LED 55 and the illumination lens 56 in the other hole and by separately providing the window portions 57 and 58 in the respective holes, the CCD 53 and the objective lens 54 are light-shielded from the white LED 55 and the illumination lens 56, thus preventing light of the white LED 55 from adversely affecting the CCD 53.

The body portion 51 has a function of fixing a positional relationship between the CCD 53 and the objective lens 54, a positional relationship between the white LED 55 and the illumination lens 56, and a positional relationship between the CCD 53 plus the objective lens 54 and the white LED 55 plus the illumination lens 56, respectively.

A control line and a signal line of the CCD 53 as well as a signal line of the white LED 55 extend through the body portion 51 and are respectively connected to corresponding terminals of the connector portion 52. The image light acquiring means is comprised of the CCD 53 and the objective lens 54, whereas the illumination means is comprised of the white LED 55 and the illumination lens 56 (the window portion 58).

In the laryngoscope 5, light (image light) reflected from the observation site just in front of or around the distal end wall 41 of the assistance instrument main body 4 forms an image on a light receiving surface (image pickup surface) of the CCD 53 through the objective lens 54. An object image (image light) thus formed is taken by the CCD 53. In other words, the CCD 53 takes an image of the observation site.

Taking a specific example, the CCD 53 can take or acquire an object image of at least an epiglottis of a patient and its vicinity at the time when the epiglottis is lifted up by means of a tongue piece 42 of the assistance instrument main body 4 and also can take an object image of at least a rima glottidis of a patient and its vicinity (a larynx and a rima glottidis) in the case where the air passage is secured by the assistance instrument main body 4.

As the white LED 55 emits light, the light is irradiated on the observation site from the distal end wall 41 of the assistance instrument main body 4 through the illumination lens 56, thereby illuminating the observation site. This makes it possible to illuminate the observation site with sufficient brightness.

Although the white LED 55 is single in the illustrated embodiment, two or more white LEDs may alternatively be used depending on a F-number of the objective lens 54 and sensitivity of the CCD 53.

In this regard, it is to be noted that the image light acquiring means is not restricted to the configuration set forth above. As an alternative example, the image light acquiring means may be comprised of, e.g., an image guide and a CCD (image pickup device) provided on a proximal end of the image guide.

The image guide may include a fiber bundle and an objective lens arranged on a distal end of the fiber bundle, for instance. The fiber bundle is formed by tying together a plurality of individual optical fibers made of, e.g., quartz, multi-component glass, plastics or the like.

In this type of image light acquiring means, the image guide picks up the light (image light) reflected from the observation site by use of the objective lens. The image light (object image) thus picked up is transmitted to the CCD via the fiber bundle and then the CCD takes the object image. In this exemplary configuration, the image guide constitutes a means for leading the image light of the observation site (object image) to the image pickup device.

The image pickup device may be installed either on the apparatus main body 2 or on the intubation assistance instrument 3. In place of the CCD, an eyepiece lens may be employed to enable an operator to observe the observation site with a naked eye.

Likewise, the illumination means is not restricted to the configuration set forth above. As an alternative example, the illumination means may be comprised of, e.g., a light guide and a white LED (light source) provided on a proximal end of the light guide.

The light guide may include a fiber bundle and an illumination lens arranged on a distal end of the fiber bundle, for instance. The fiber bundle may be made of the same material as that of the fiber bundle of the image guide noted above.

In this type of illumination means, the light guide leads therethrough the light emitted from the white LED and irradiates the light on the observation site at the distal end wall 41 of the assistance instrument main body 4, thereby illuminating the observation site.

In this exemplary configuration, the light guide constitutes a means (light guide means) for leading the light from the light source to the distal end wall 41 of the assistance instrument main body 4. The light source may be installed either on the apparatus main body 2 or on the intubation assistance instrument 3.

The intubation assistance instrument 3 is mounted to the apparatus main body 2. This intubation assistance instrument 3 includes an assistance instrument main body 4 that has various additional functions set forth below as well as a function equivalent to that of a typical oral airway, a guide member 8 detachably attached to the assistance instrument main body 4 and a lock mechanism 9 for removably locking the guide member 8 to the assistance instrument main body 4 provided on the assistance instrument main body 4.

The intubation assistance instrument 3 is used in a state that the guide member 8 is attached to a side portion of the assistance instrument main body 4 and locked to the assistance instrument main body 4 by the lock mechanism 9. Hereinafter, this state is referred to as "guide member-locking state".

The assistance instrument main body 4 is formed of an elongated member. This assistance instrument main body 4 is mounted to the apparatus main body 2 and inserted into a target site, namely, a trachea of a patient or its vicinity, from a mouth (mouth cavity) of the patient. By way of example, the assistance instrument main body 4 is used in such a manner that it is inserted through a mouth of a patient who has lost consciousness or who is under general anesthesia.

An air passage for the patient is secured by bringing an appropriate portion on the side of a distal end of the assistance instrument main body 4 into contact with a root of a tongue of the patient, while lifting up an epiglottis of the patient by use of a below-mentioned tongue piece (protruding portion) 42 formed on the side of the distal end of the assistance instrument main body 4.

As illustrated in FIGS. 1 and 2, the assistance instrument main body 4 is curved at a roughly middle part thereof so that a distal end side extension thereof can be oriented in a lateral direction in FIG. 1, thereby forming a curved portion 40. A proximal end side extension of the curved portion 40 makes a generally right angle with respect to the distal end side extension thereof.

In this embodiment, the assistance instrument main body 4 (intubation assistance instrument 3) has optical transparency in its entirety. Alternatively, only a required portion (area) of the assistance instrument main body 4 may be optically transparent.

On the distal end wall 41 of the assistance instrument main body 4, there is a plate-like tongue piece (protruding portion) 42 that protrudes in a frontward direction and has optical transparency. The tongue piece 42 is formed so as to continuously extend from a curved inner side 401 of the curved portion 40 at the distal end portion of the assistance instrument main body 4.

During a course of an intubation operation, an epiglottis of a patient can be lifted up with the tongue piece 42 to thereby secure an air passage for the patient in an easy and reliable manner. In this regard, it is to be noted that the distal end wall 41 of the assistance instrument main body 4 is inclined with respect to the tongue piece 42.

As shown in FIG. 7, the tongue piece 42 is of a generally rectangular shape when viewed from the top thereof. Moreover, corner portions of the tongue piece 42 are rounded to improve safety in the process of insertion. The shape of the tongue piece 42 as seen from the top thereof is not restricted to a rectangular one, but may be of other shapes, e.g., a semi-elliptical shape or a semi-circular shape.

Further, as shown in FIGS. 1 and 2, a side wall 48 is formed on the assistance instrument main body 4 and is integrally joined to (formed with) the distal end wall 41 and the tongue piece 42.

As shown in FIG. 6, in the guide member-locking state, the assistance instrument main body 4 (intubation assistance instrument 3) has a generally rectangular cross-section near the distal end wall 41 thereof.

Further, in a cross section of the distal end wall 41 of the assistance instrument main body 4, a width "w" thereof is preferably in the range of about 15 to 40 mm, and more preferably in the range of about 25 to 30 mm, whereas a thickness "t" thereof is preferably in the range of about 10 to 30 mm, and more preferably in the range of about 15 to 20 mm.

By setting the width "w" and the thickness "t" to values within the above ranges, the intubation assistance instrument 3 can be inserted into the patient easily and promptly during the course of the intubation operation, thus reducing burden on the patient.

Further, when the distal end wall 41 of the assistance instrument main body 4 is brought into contact with (or pressed against) the root portion of the tongue during the course of the intubation operation, the tongue piece 42 having a plate-like shape makes it possible to prevent the tongue of the patient from being hung down to the side of the distal end wall 41 of the assistance instrument main body 4. Therefore, it is possible to prevent a field of view of the CCD 53 from being narrowed.

In this regard, it is to be noted that the cross-section of the distal end wall 41 of the assistance instrument main body 4 is not restricted to the rectangular shape, but may have other shapes, e.g., an elliptical shape, a semi-elliptical shape, a circular shape, a semi-circular shape or the like.

As described above, formed on the assistance instrument main body 4 is the scope guide bore 44 that extends from the proximal end portion to the distal end wall 41, namely, along the longitudinal direction of the assistance instrument main body 4, and serves as the disposing portion on which at least a part (the entirety in this embodiment) of the laryngoscope 5 is disposed.

In this connection, the distal end portion (the entirety in this embodiment) of the scope guide bore 44 is eccentrically located in a width direction of the tongue piece 42.

The scope guide bore 44 has a cross-section of a generally circular shape and is opened at the proximal end portion of the assistance instrument main body 4. The proximal end side of the scope guide bore 44 is fluid-tightly (air-tightly) sealed under the state that the intubation assistance instrument 3 is mounted to the apparatus main body 2.

Further, the distal end of the assistance instrument main body 4 is closed by the distal end wall 41.

In this regard, as shown in FIG. 7, the distal end portion of the scope guide bore 44 is slanted toward the intubation tube 200 inserted into the guide member 8 (toward the guide member 8). In other words, the scope guide bore 44 is inclined with respect to a center line 47 of the distal end wall 41 of the assistance instrument main body 4 in such a manner that a center line 59 of a visual field of the CCD (image light acquiring means) 53 of the laryngoscope 5 disposed or received in the scope guide bore 44 can be headed for the intubation tube 200 (the guide member 8).

By such a structure, in the intubation operation during which the intubation tube 200 is pushed forward from the distal end wall 41 of the assistance instrument main body 4, the intubation tube 200 is adapted to advance toward substantially a center of a screen image displayed by the display 71.

This allows an operator to quite easily ascertain, in the intubation operation, a positional relationship between the rima glottidis, which is an entrance of the trachea, and the distal end portion of the intubation tube 200 with seeing the screen image displayed on the display 71.

As shown in FIG. 7, formed through the assistance instrument main body 4 is an internal bore (lumen) 46 that extends from the proximal end portion to the distal end wall 41, namely, along the longitudinal direction of the assistance instrument main body 4.

In this connection, a distal end of the internal bore 46 lies on the side of the tongue piece 42 between the guide member 8 and the scope guide bore 44. Further, the distal end of the internal bore 46 is opened on the distal end wall 41 of the assistance instrument main body 4.

Inside the internal bore 46, there is provided a suction tube, a forceps or the like not shown in the drawings, for example. The suction tube or the forceps may be detachably fitted into or fixedly secured to the internal bore 46. Use of the suction tube makes it possible to suck up and remove flowable foreign materials such as spit, sputum and so forth. Solid foreign materials can be removed using the forceps.

Although the internal bore 46 is formed in a single number in the illustrated embodiment, two or more internal bores may be provided alternatively.

As described above, the guide member 8 is detachably attached to the side portion of the assistance instrument main body 4. This guide member 8 is formed of an elongated member as well as the assistance instrument main body 4, and has a curved portion 81 formed by curving it at its longitudinal midway part.

In the guide member-locking state shown in FIG. 1, a curved degree of the curved portion 81 of the guide member 8 corresponds to that of the curved portion 40 of the assistance instrument main body 4.

As shown in FIGS. 1 to 3, the guide member 8 includes a body portion 80 having a plate shape, a guide portion (a guide member side tube restriction portion) 82 into which the intubation tube 200 is to be inserted, a lock portion 83 which is to be locked by the lock mechanism 9, and a rib (protruding portion) 84 which is to be engaged with the assistance instrument main body 4.

The guide portion 82 is provided on one surface of the body portion 80, that is, a surface of the body portion 80 opposite to the assistance instrument main body 4 in the guide member-locking state. In the guide member-locking state, when the intubation tube 200 is inserted into the guide portion 82, it can be guided toward a desired site of the patient through the guide portion 82.

As shown in FIGS. 1, 3 and 6, the guide portion 82 has a cross-section of a circular arc shape (U-like shape). By such a structure, a recess (groove) 821 is formed inside the guide portion 82 so as to extend along the longitudinal direction of the assistance instrument main body 4. Further, the recess 821 is opened on a curved inner side of the curved portion 81.

In such a guide member 8, the intubation tube 200 can be inserted into the recess 821 (see, FIG. 1). A width (maximum width) of the recess 821 is set to have a dimension slightly greater than an outer diameter of the intubation tube 200. This makes it possible to easily insert (intubate) the intubation tube 200 into the recess 821.

In a general method of using the intubation assistance apparatus 1, an operator initially takes a position on the upper side of a head of a lying-down patient and, subsequently, the intubation assistance apparatus 1 is placed so that a display 71 provided in the intubation assistance apparatus 1 can face the operator as shown in FIG. 8.

In the case where the operator, the patient and the intubation assistance apparatus 1 are in such a positional relationship (namely, an in-use positional relationship), the guide portion 82 (recess 821) lies on the right side of the assistance instrument main body 4 when viewed from the operator.

Under the state that the air passage is secured by the assistance instrument main body 4, the guide portion 82 serves to guide the intubation tube 200 toward the trachea of the patient as it is inserted through the mouth of the patient. Further, the intubation tube 200 can be easily removed from the guide portion 82 while the insertion section 4 remains inserted into a body of the patient.

Once the air passage for the patient is secured by the assistance instrument main body 4, the intubation tube 200 is introduced into the guide portion 82 at a proximal end portion thereof and then continues to be pushed toward the distal end portion 41 of the assistance instrument main body 4. At this time, the intubation tube 200 is guided by at least an inner wall 822 of the guide portion 82 and is moved forward while making sliding contact with the inner wall 822.

Then, the distal end of the intubation tube 200 continues to be moved toward the rima glottidis in the back of the larynx beyond the distal end of the guide portion 82. In this process, the guide portion 82 lies on the right side of the assistance instrument main body 4 when viewed from the operator and therefore the operator can operate the intubation tube 200 with his or her right hand in the same manner as is done in the video laryngoscope.

In this regard, it is preferred that the inner surface 822 of the guide portion 82 is subjected to a treatment of decreasing friction between the inner surface 822 and the intubation tube 200 inserted into the guide portion 82. This makes it possible to easily carry out the intubation operation.

Examples of such a treatment includes, but are not limited to, a treatment of coating the inner surface 822 with fluorine, a treatment of forming fine irregularities onto the entirety of the inner surface 822, and the like.

As shown in FIGS. 1 and 6, in the guide member-locking state, a tube restriction portion (main body side tube restriction portion) 49 of the assistance instrument main body 4 prevents the intubation tube 200 inserted into the guide portion 82 from being removed from the recess 821 of the guide portion 82 through the opening thereof.

In other words, in the guide member-locking state, the intubation tube 200 inserted into the guide portion 82 is held between the guide portion 82 and the tube restriction portion 49 of the assistance instrument main body 4, so that radial move of the intubation tube 200 is restricted.

This makes it possible to prevent the intubation tube 200 from being undesirably removed from the guide portion 82 during the course of the intubation operation. As a result, it is possible to reliably prevent the intubation tube 200 from being not reached to the desired site of the patient.

In this regard, it is to be noted that the tube restriction portion 49 is composed of a rib (wall portion) which is protruded from the assistance instrument main body 4 and formed so as to extend from the curved inner side 401 of the curved portion 40 of the assistance instrument main body 4 in a width direction thereof.

In the guide member-locking state, this rib can cover the recess 821 of the guide portion 82 from the opening side thereof. This makes it possible to reliably prevent the intubation tube 200 from being removed from the guide portion 82.

A clearance "h" between the tube restriction portion 49 of the assistance instrument main body 4 and the guide portion 82 of the guide member 8 corresponds to the outer diameter of the intubation tube 200, and specifically, is set to have a dimension substantially equal to or slightly greater than the outer diameter of the intubation tube 200.

As shown in FIGS. 3 and 6, a rib 84 is formed so as to protrude from the other surface of the body portion 80, that is, a surface of the body portion 80 opposite to the surface on which the guide portion 82 is provided. This rib 84 is a portion which is to be engaged with the assistance instrument main body 4 in the guide member-locking state.

This rib 84 is composed of a first rib 841 formed so as to extend along the longitudinal direction of the body portion 80 (guide member 8) and a second rib 842 formed so as to extend along the width direction of the body portion 80.

The first rib 841 is provided along an edge of the body portion 80. The first rib 841 has a cross-section of a L-like shape. The second rib 842 is provided at a distal end of the first rib 841 and is continuously (integrally) formed therewith. The second rib 842 has a cross-section of a T-like shape.

As shown in FIG. 2, a groove 43 into which the rib 84 is to be inserted is formed on the assistance instrument main body 4 so as to correspond to the rib 84 in the guide member-locking state. The groove 43 is composed of a first groove 431 into which the first rib 841 is to be inserted and a second groove 432 into which the second rib 842 is to be inserted.

The first groove 431 has a cross-section of a L-like shape as well as the first rib 841, and allows the first rib 841 to be inserted thereinto. The second groove 432 has a cross-section of a T-like shape as well as the second rib 842, and allows the second rib 842 to be inserted thereinto.

As shown in FIG. 2, in the intubation assistance instrument 3, in the case where the guide member 8 is attached to the assistance instrument main body 4, the first rib 841 slides along (is inserted into) the first groove 431 and the second rib 842 of the guide member 8 is inserted into the second groove 432 of the assistance instrument main body 4.

In this case, an attaching direction of the guide member 8 to the assistance instrument main body 4 becomes a direction toward the proximal end of the assistance instrument main body 4 from the distal end thereof. On the other hand, in the case where the guide member 8 attached to the assistance instrument main body 4 is detached therefrom, a detaching direction becomes a direction opposite to the above attaching direction.

In such an intubation assistance instrument 3, the attaching and detaching direction (moving direction) of the guide member 8 to the assistance instrument main body 4 is restricted. Therefore, even if the assistance instrument main body 4 is mounted to the apparatus main body 2, the attaching and detaching operation by which the guide member 8 is attached to and detached from the assistance instrument main body 4 can be carried out at the side opposite to the apparatus main body 2.

This makes it possible to prevent the apparatus main body 2 from disturbing the attaching and detaching operation, thereby easily carrying out this attaching and detaching operation. In the intubation assistance instrument 3, the rib 84 of the guide member 8 and the groove 43 of the assistance instrument main body 4 serve as a restriction means 32 of restricting the attaching and detaching direction of the guide member 8.

As shown in FIGS. 2 to 5, the lock portion 83 is provided on the proximal end portion of the body portion 80. This lock portion 83 is locked and unlocked with the lock mechanism 9 so that the guide member 8 is detachably attached to the assistance instrument main body 4.

The lock portion 83 is composed of defective portions 831 each formed by removing a part of the edge of the body portion 80. Further, chamfer portions 832 are formed by chamfering both corner portions of the proximal end portion of the body portion 80.

In this regard, it is to be noted that the locking and unlocking state of the lock portion 83 with the lock mechanism 9 will be described below.

In the guide member 8 having such a structure, the body portion 80, the guide portion 82, the lock portion 83 and the rib 84 may be integrally formed together, or may be composed of separated parts, respectively, and joined together.

Further, examples of a constituent material of the guide member 8 include, but are not limited to, various kinds of thermoplastic resins such as polyethylene and polypropylene and various kinds of metal materials such as stainless steel.

The guide member 8 is locked to the assistance instrument main body 4 by the lock mechanism 9.

As shown in FIGS. 1 and 2, the lock mechanism 9 is provided on the assistance instrument main body 4 near the proximal end portion thereof. As shown in FIGS. 4 and 5, the lock mechanism 9 includes a pair of engagement members 91 provided so as to face to each other, a coil spring (bias portion) 92 that biases the engagement members 91 so as to come close to each other, and a cover 93 that covers the engagement members 91 and the coil spring 92.

The pair of engagement members 91 mutually have the same structures. Therefore, a description will be, representatively, made on one of the engagement members 91.

The engagement member 91 is formed from an elongated plate member. The engagement member 91 is rotatably supported (attached) to the assistance instrument main body 4 at its midway part. This midway part of the engagement member 91 serves as a rotatable support portion 913. By such a structure, the engagement member 91 can be rotated around the rotatable support portion 913 which serves as a supporting point (center) (see, FIGS. 4 and 5).

The rotatable support portion 913 is not limited to a specific type. For example, the rotatable support portion 913 is composed of a bearing (through hole) which is formed so as to pass through the engagement member 91 in a thickness direction thereof and into which a shaft formed so as to protrude from the assistance instrument main body 4 can be fitted.

The engagement member 91 has an engagement portion 911 provided on the distal end thereof and an operation portion 912 provided on the proximal end thereof.

The engagement portion 911 of one of the engagement portions 911 is formed so as to extrude toward the other engagement member 91 faced to the one engagement member 91. Each engagement member 91 can be rotated around the rotatable support portion 913. Therefore, the engagement portion 911 of the one engagement member 91 can come close to the engagement portion 911 of the other engagement member 91 and separate therefrom.

As shown in FIG. 4, in a state that the engagement portions 911 come close to each other, they can become engaged with the defective portions 831 of the lock portion 83 of the guide member 8. Further, the engagement portion 911 has an inclined portion 914 which is formed so as to be inclined with respect to the attaching direction (attaching and detaching direction) of the guide member 8 at the distal end portion thereof.

In the case where the guide member 8 is locked to the assistance instrument main body 4 by the lock mechanism 9, the guide member 8 is approached to the lock mechanism 9 from the side of the lock portion 83. At this time, the chamfer portions 832 of the lock portion 83 of the guide member 8 slide on the inclined portions 914 of the engagement portions 911, and therefore they pushes the engagement portions 911 outward against biasing force of the coil spring 92 and widens a distance therebetween.

When the chamfer portions 832 pass through between the engagement portions 911, the engagement portions 911 can become engaged with the defective portions 831 of the lock portion 83 of the guide member 8.

As described above, according to the intubation assistance instrument 3, by a simple operation in which the guide member 8 is merely inserted into the assistance instrument main body 4, the guide member 8 can be attached to the assistance instrument main body 4. Therefore, the intubation assistance instrument 3 exhibits excellent operationality.

Further, the entirety of the attached guide member 8 is supported and fixed to the assistance instrument main body 4 along the longitudinal direction thereof by the actuation of the lock mechanism 9 and the restriction means 32. This makes it possible to reliably prevent occurrence of displacement of the guide member 8 to the assistance instrument main body 4 during a course of an operation of the intubation assistance apparatus 1.

The operation portion 912 is formed so as to protrude in a direction opposite to the protruding direction of the engagement portion 911. As shown in FIG. 5, when this operation portion 912 is pushed in an arrow direction shown in FIG. 5, the operation portions 912 separate from the defective portions 831 of the lock portion 83 of the guide member 8. In this way, it is possible to carry out an operation of unlocking the engagement between the guide member 8 and the engagement members 91.

Further, this unlock (release) operation cannot be carried out, if the operation portions 912 of the engagement members 91 are not pushed together. Therefore, even if one of the operation portions 912 is improperly pushed during the use (operation) of the intubation assistance apparatus 1, the engagement state between the lock mechanism 9 and the guide member 8 is maintained unless the other operation portion 912 is pushed. As a result, the separation of the guide member 8 from the assistance instrument main body 4 is prevented.

Both ends 921 of the coil spring 92 are connected to predetermined portions of the engagement members 91 closer to the distal ends thereof than the rotatable support portions 913, respectively. By this structure, the coil spring 92 can bias the engagement members 91 so that the engagement portions 911 come close to each other.

Therefore, when the engagement portions 911 become engaged to the defective portions 831 of the lock portion 83 of the guide member 8, it is possible to reliably prevent the engagement state from being undesirably unlocked (see, FIG. 4). This makes it possible to reliably fix (secure) the guide member 8 to the assistance instrument main body 4.

On the other hand, as described above, the unlock operation of the engagement state is carried out by pushing the operation portions 912 of the engagement members 91 together against the biasing force of the coil spring 92. The guide member 8 can be removed from the lock mechanism 9 by pulling the guide member 8 toward the distal end direction thereof.

The lock mechanism 9 has conflicting functions, that is, both a function of reliably locking the guide member 8 and a function of easily unlocking the guide member 8.

Since the guide member 8 is attached to and detached from the assistance instrument main body 4 at the side opposite to the apparatus main body 2 through the lock mechanism 9, the attaching and detaching operation can be carried out in a state that the assistance instrument main body 4 is mounted to the apparatus main body 2.

This makes it possible to prevent the apparatus main body 2 from disturbing the attaching and detaching operation of the guide member 8 which will be described below, thereby easily carrying out this attaching and detaching operation.

As show in FIGS. 1 and 2, the cover 93 is composed of a plate member having a square shape when viewed from the top thereof. A plurality of spacers 931 are formed on a rear surface of the cover 93 so as to protrude therefrom. This structure makes it possible to create a gap 932 between the rear surface of the cover 93 and the assistance instrument main body 4 (see, FIG. 1).

The engagement members 91 and the coil spring 92 are positioned within the gap 932. This makes it possible to reliably prevent fingers or the like from being undesirably caught in the engagement members 91 or the coil spring 92. Therefore, safety during the course of the operation of the lock mechanism 9 is ensured. In this embodiment, the cover 93 is secured on the assistance instrument main body 4 using three bolts 94.

Examples of a constituent material of each of the engagement members 91, the coil spring 92 and the cover 93 include, but are not limited to, various kinds of metal materials such as stainless steel.

Depending to patients or manipulations, the intubation assistance instrument 3 having the above structure may be selectively used by attaching the guide member 8 to the assistance instrument main body 4 or by not attaching the guide member 8 to the assistance instrument main body 4 (that is, as the assistance instrument main body 4 alone).

For example, in the case where the intubation assistance instrument 3 is used for patients having mouths with substantially small sizes such as infants, for a tracheal intubation or other manipulations, it can be used by not attaching the guide member 8 to the assistance instrument main body 4.

On the other hand, in the case where the intubation assistance instrument 3 is used for patients having mouths with substantially large sizes such as adults, it can be used by attaching the guide member 8 to the assistance instrument main body 4.

A description will now be given to one exemplary use (operation) of the intubation assistance apparatus 1. Hereinbelow, a case that the intubation assistance instrument 3 in the guide member-locking state is used will be described.

The intubation assistance apparatus 1 is used in such an instance that a patient has lost consciousness and a need exists to insert the intubation tube 200 into a trachea of the patient.

[1] First, the intubation assistance apparatus 1 is assembled in preparation for insertion of the intubation tube 200.

To this end, the connector portion 52 of the laryngoscope 5 is first connected to the connector portion 61 of the apparatus main body 2. If needed, a suction tube, for example, is inserted into and installed within the internal bore 46 of the assistance instrument main body 4 of the intubation assistance instrument 3.

Subsequently, the laryngoscope 5 is inserted through the scope guide bore 44 of the assistance instrument main body 4 of the intubation assistance instrument 3 and, at the same time, the proximal end portion 31 of the assistance instrument main body 4 is inserted between the coupling portion 23 and the operating sleeve 24 of the casing 21 of the apparatus main body 2. Then, the operating sleeve 24 is rotated in a predetermined direction, thereby mounting the assistance instrument main body 4 to the apparatus main body 2.

Thereafter, the guide member 8 is attached to the assistance instrument main body 4 in the same manner as described above, to thereby bring into the guide member-locking state. This attaching operation can be easily carried out by the restriction means 32 and the lock mechanism 9.

[2] Next, the individual parts (the white LED 55, the CCD 53, the display 71 and so forth) of the intubation assistance apparatus 1 are driven by operating switches not shown in the drawings, and the assistance instrument main body 4 of the intubation assistance instrument 3 in the guide member-locking state is pushed into the trachea of the patient through his or her mouth.

More specifically, the assistance instrument main body 4 is inserted into a mouth of the patient, while allowing the curved inner side 401 of the curved portion 40 of the assistance instrument main body 4 to extend along a root of a tongue.

Seeing and ascertaining an image displayed on the display 71, an operator lifts up an epiglottis of the patient toward the root of the tongue with the tongue piece 42 of the assistance instrument main body 4. Then, an appropriate area of the distal end side of the assistance instrument main body 4 is brought into contact with the tongue root portion of the patient, thus securing an air passage.

Since the tongue piece 42 (assistance instrument main body 4) is optically transparent, the CCD 53 can take an image of the epiglottis through the tongue piece 42 at the time when the epiglottis of the patient is lifted up toward the root of the tongue with the tongue piece 42.

The image thus taken is displayed on the display 71. Further, since the tongue piece 42 has a plate-like shape, the epiglottis can be lifted up by means of the tongue piece 42 in an easy, speedy and reliable manner. This makes it possible to secure the air passage in an easy, speedy and reliable fashion.

[3] Once the air passage is secured by the distal end of the assistance instrument main body 4, the intubation tube 200 is inserted into the guide portion 82 from the proximal end portion of the assistance instrument main body 4 and continues to be pushed forward. In this process, the intubation tube 200 is guided by the guide portion 82 and moved forward along the guide portion 82.

Observing the image displayed on the display 71 (including the image of the distal end portion of the intubation tube 200), the operator inserts the distal end portion of the intubation tube 200, which protrudes from the guide portion 82, into a rima glottidis so that it can reach the trachea.

In this regard, the guide portion 82 is shaped to ensure that the distal end portion of the intubation tube 200 naturally moves toward the rima glottidis. Thus, the intubation tube 200 is leaded to the rima glottidis by itself.

In this way, the operator can insert the intubation tube 200 from the rima glottidis into the trachea while seeing the image displayed on the display 71, and the intubation tube 200 is naturally leaded to the rima glottidis by the guide portion 82. Accordingly, it is possible for the operator to insert the intubation tube 200 into the trachea in an easy, speedy and reliable fashion.

[4] Under the state that the intubation tube 200 remains inserted into the trachea, the intubation tube 200 is deformed and removed from the guide portion 82.

[5] While maintaining this condition, the assistance instrument main body 4 is removed or taken out from the mouth of the patient. In this way, the intubation tube 200 can be intubated into the trachea of a patient.

Thereafter, the intubation tube 200 is connected at its proximal end to an artificial respiration device which in turn supplies the air into the trachea through the intubation tube 200 inserted into the trachea from the rima glottidis.

As described above, according to the intubation assistance apparatus 1, the guide member can be easily attached to and detached from the assistance instrument main body using a simple manner such as the activation of the lock mechanism. That is, the intubation assistance instrument 3 can be separated into the assistance instrument main body 4 and the guide member 8. Further, the intubation assistance instrument 3 is detachably mounted to the apparatus main body 2.

By such a structure, the assistance instrument main body 4 and the guide member 8 can be separately subjected to cleansing, disinfecting and sterilizing processes. Further, detailed portions such as the groove 43 of the assistance instrument main body 4, and the guide portion 82 of the guide member 8 also can be subjected to the cleansing, disinfecting and sterilizing processes reliably.

Even in the case where the assistance instrument main body 4 and the guide member 8 are reused, it is possible to keep the patient from being infected (secondarily infected) by bacteria, which helps to enhance the safety.

Further, since the intubation tube 200 slides on the guide portion 82 of the guide member 8, the guide member 8 tends to be easily abraded among parts constituting the intubation assistance apparatus 1. That is, the guide member 8 is a consumable. In the intubation assistance apparatus 1, the consumable is detachable. Therefore, the consumed guide member 8 can be exchanged to another new guide member 8.

Next, a description will be made on another configuration example of such an intubation assistance apparatus 1. In this structural example, the intubation assistance apparatus 1 includes the guide members 8 of various types (three types in FIGS. 11A to 11C) each having the above structure.

FIGS. 11A to 11C are perspective views illustrating guide members of three types each included in the intubation assistance instrument shown in FIG. 1. In the following description, the lower side and the upper side in FIGS. 11A to 11C will be referred to as "distal end" and "proximal end", respectively, for the purpose of clarity.

As shown in FIGS. 11A to 11C, each of guide members 8A to 8C can guide a corresponding intubation tube among intubation tubes 200A to 200C having different outer diameters. Namely, guide portions 82 of the guide members 8A to 8C have different widths and depths (shapes and sizes). The guide portion 82 of each guide member 8A, 8B or 8C has the size suitable for the intubation tube 200A, 200B or 200C which is to be inserted thereinto (intubated).

As described above, in the guide member-locking state, the intubation assistance instrument 3 can hold each intubation tube 200A, 200B or 200C between the guide portion 82 of each guide member 8A, 8B or 8C and the tube restriction portion 49 of the assistance instrument main body 4.

By appropriately selecting one of the guide members of three types 8A to 8C and using it, it is possible to set a clearance "h" between the tube restriction portion 49 of the assistance instrument main body 4 and the guide portion 82 of the selected guide member 8A, 8B or 8C to a predetermined value. This makes it possible for intubation assistance instrument 3 to hold each of the intubation tubes 200A to 200C having the different outer diameters.

Among the three guide members 8A to 8C, the guide portion 82 of the guide member 8A shown in FIG. 11A has largest width and depth. This guide member 8A can guide the intubation tube 200A having a largest outer diameter.

Further, the guide portion 82 of the guide member 8C shown in FIG. 11C has smallest width and depth. This guide member 8C can guide the intubation tube 200C having a smallest outer diameter.

Furthermore, the guide portion 82 of the guide member 8B shown in FIG. 11B has middle width and depth which are in between the width and depth of the guide portion 82 of the guide member 8A and the width and depth of the guide portion 82 of the guide member 8C. This guide member 8B can guide the intubation tube 200B having a middle outer diameter which is in between the diameter of the intubation tube 200A and the diameter of the intubation tube 200C.

One of the three guide members 8A to 8C can be selected, and be attached to the assistance instrument main body 4. A description will now be given to one exemplary use (operation) of such an intubation assistance apparatus 1.

[1'] First, one of the intubation tubes 200A to 200C is selected depending on a patient. For example, in the case where the intubation tube 200B is selected, the intubation assistance apparatus 1 is assembled using the guide member 8B in preparation for insertion of the intubation tube 200B.

The laryngoscope 5 is connected to the apparatus main body 2 and the assistance instrument main body 4 of the intubation assistance instrument 3 are mounted thereto in the same manner as described above.

[2'] Thereafter, the guide member 8B is attached to the assistance instrument main body 4 in the same manner as described above to thereby bring into the guide member-locking state.

[3'] Next, the intubation assistance instrument 3 is pushed into a trachea of a patient through his or her mouth in the same manner as described above.

[4'] Once the air passage is secured by the distal end of the assistance instrument main body 4, the intubation tube 200B is inserted into the guide portion 82 from the proximal end portion of the assistance instrument main body 4 and continues to be pushed forward in the same manner as described above. In this process, the intubation tube 200B is guided by the guide portion 82 and moved forward along the guide portion 82.

Here, if the selected intubation tube 200B is incompatible to the patient, it cannot be inserted into a rima glottidis, and therefore it cannot reach the trachea. In this case, the intubation tube 200B needs to be exchanged to another intubation tube 200A or 200C. In this operation, the intubation tube 200B is exchanged to the intubation tube 200C.

At this time, the individual parts of the intubation assistance apparatus 1 are stopped by operating the above switches. Thereafter, the intubation tube 200B is removed from the guide member 8B, and then the assistance instrument main body 4 to which the guide member 8B is attached is once removed from the mouth of the patient.

[5'] Next, in the state that the assistance instrument main body 4 is mounted to the apparatus main body 2, the unlock operation of the lock mechanism 9 is carried out as described above. Thereafter, the guide member 8B is detached from the assistance instrument main body 4.

[6'] After the guide member 8B has been detached from the assistance instrument main body 4, the guide member 8C is attached to the assistance instrument main body 4 in the same manner as the guide member 8B.

[7'] Next, the individual parts of the intubation assistance apparatus 1 are driven by re-operating switches, and the assistance instrument main body 4 of the intubation assistance instrument 3 in the guide member-locking state is pushed into the trachea of the patient through his or her mouth.

[8'] Subsequently, the air passage is secured by the distal end of the assistance instrument main body 4, the intubation tube 200C is inserted into the guide portion 82 from the proximal end portion of the assistance instrument main body 4 in the same manner as described above. Thereafter, the operator inserts the distal end portion of the intubation tube 200C into the rima glottidis so that it can reach the trachea.

[9'] Under the state that the intubation tube 200C remains inserted into the trachea, the intubation tube 200C is deformed and removed from the guide portion 82.

[10'] While maintaining this condition, the assistance instrument main body 4 is removed or taken out from the mouth of the patient. In this way, the intubation tube 200C can be intubated into the trachea of a patient.

Thereafter, the intubation tube 200C is connected at its proximal end to an artificial respiration device which in turn supplies the air into the trachea through the intubation tube 200C inserted into the trachea from the rima glottidis.

As described above, according to the intubation assistance apparatus 1, in the case where the operator wants to exchange the intubation tube 200B to the intubation tube 200C during the use of the intubation assistance apparatus 1, the operator can exchange the guide member 8B to the guide member 8C while maintaining the state that the assistance instrument main body 4 is mounted to the main body 2.

And then, the operator can insert the intubation tube 200C into the mouth of the patient using the exchanged guide member 8C. Therefore, the exchange operation of the intubation tube can be rapidly carried out. Further, use of the intubation assistance apparatus 1 makes it possible to shorten the time required in the intubation operation, thus reducing burden on the patient.

Further, as described above, each of the guide members 8A to 8C can be easily attached to and detached from the lock mechanism 9. Therefore, this contributes to the rapid exchange operation of the intubation tube. In addition, each of the guide members 8A to 80 can be more easily locked and unlocked with the lock mechanism 9 by the restriction means 32.

Further, in the intubation assistance instrument 3 described above, the single assistance instrument main body 4 is shared by the plurality of guide members 8A to 8C which are prepared so as to correspond to the intubation tubes 200A to 200C having the different outer diameters. Such a structure makes it possible to lower the cost of manufacturing the intubation assistance instrument 3.

While the intubation assistance instrument, the intubation assistance apparatus and the intubation assistance system of the present invention have been described hereinabove in respect of the illustrated embodiment, this is not intended to limit the scope of the present invention.

Instead, each component or element of the intubation assistance instrument, the intubation assistance apparatus and the intubation assistance system may be replaced with other one that exhibits the same or similar function. Furthermore, other arbitrary components than disclosed above may be added thereto.

Although the intubation assistance instrument (assistance instrument main body) can be inserted into a target site, that is, the trachea of the patient, from the mouth of the patient, it may be inserted from a nasal cavity of the patient.

For example, the apparatus main body may be provided with an electronic data transmission device for transmitting an image data through a telecommunications network to a hospital to which the patient is to be transported. This allows hospital employees to prepare medical attendance for the patient during the transportation of the patient by an ambulance car.

Further, unlike the above-noted embodiment wherein the assistance instrument main body of the intubation assistance instrument is detachably mounted to the apparatus main body, the intubation assistance instrument may be fixedly secured to the apparatus main body.

Furthermore, the cross-sectional shape of the guide portion of the guide member is not limited to the circular arc shape. Other examples of the cross-sectional shape of the guide portion include an angular U-like shape. Although the guide portion is formed from the recess, it may be formed from, for example, a through-hole.

Moreover, although the restriction means for restricting the attaching and detaching direction of the guide member is composed of the rib formed on the guide member and the groove formed on the assistance instrument main body, it may be composed of, for example, a rib formed on the assistance instrument main body and a groove formed on the guide member.

In addition, the structure of the lock mechanism is not limited to one shown in the drawings. The lock mechanism may be formed using magnets, bolts (screw cramps) or the like.

Finally, it is also to be understood that the present disclosure relates to subject matters contained in Japanese Patent Applications Nos. 2009-120253 and 2009-120254 both filed on May 18, 2009 which are expressly incorporated herein by reference in their entireties.

What is claimed is:

1. An intubation assistance instrument, comprising:
    an elongated assistance instrument main body to be inserted into a target site of a patient from a mouth cavity or a nasal cavity of the patient, the assistance instrument main body having a first side portion, a second side portion opposite to the first side portion and a tube restriction portion defined by a rib that protrudes from the first side portion;
    a guide member detachably attached on the first side portion of the assistance instrument main body, the guide member having an elongated shape and a guide portion into which an intubation tube is to be inserted when the intubation tube is intubated into the target site of the patient, the guide portion capable of guiding the intubation tube to the target site; and
    a lock mechanism that locks the guide member on the first side portion of the assistance instrument main body when the guide member is attached on the first side portion of the assistance instrument main body, the lock mechanism provided on the first side portion of the assistance instrument,
    wherein the guide portion comprises a recess which has an inner wall, and wherein the recess is formed so as to extend along a longitudinal direction of the guide member, wherein when the guide member is attached on the first side portion of the assistance instrument main body, the tube restriction portion of the assistance instrument main body and the inner wall of the recess are configured to form an opened channel extending in a direction along the longitudinal direction of the guide member, and
    wherein the opened channel is configured to hold the intubation tube in a manner such that the intubation tube is removable from the guide portion in a direction perpendicular to the extending direction of the opened channel and away from the first side portion of the assistance instrument main body.

2. The intubation assistance instrument as claimed in claim 1, wherein the intubation assistance instrument is configured to selectively intubate one of intubation tubes having different outer diameters,
    wherein the intubation assistance instrument comprises, as the guide member, a plurality of guide members each having a guide portion with a shape and a size corresponding to the outer diameter of the intubation tube to be inserted into the guide portion, and wherein one of the plurality of guide members is selected depending on the intubation tube to be intubated into the target site, and the selected guide member is detachably attached on the first side portion of the assistance instrument main body.

3. The intubation assistance instrument as claimed in claim 1, wherein the lock mechanism includes: a pair of engagement portions provided in a mutually facing relationship so as to come close to and separate from each other, the engagement portions capable of engaging with the guide member; a bias portion that biases the engagement portions so that they come close to each other; and operation portions that are operated for unlocking the engagement between the engagement portions and the guide member against biasing force of the bias portion.

4. The intubation assistance instrument as claimed in claim 3, wherein each of the engagement portions is rotatably attached to the assistance instrument main body.

5. The intubation assistance instrument as claimed in claim 3, wherein each of the engagement portions has an inclined portion inclining with respect to an attaching direction of the guide member to the assistance instrument main body.

6. The intubation assistance instrument as claimed in claim 1, wherein the guide member is attached on and detached from the first side portion of the assistance instrument main body by moving the guide member along a longitudinal direction of the assistance instrument main body, and wherein the intubation assistance instrument further comprises a restrictor that restricts a moving direction of the guide member.

7. The intubation assistance instrument as claimed in claim 6, wherein the restrictor comprises a groove provided on the first side portion of the assistance instrument main body and a protruding portion inserted into the groove and provided on the guide member.

8. The intubation assistance instrument as claimed in claim 1, wherein an inner surface of the recess is subjected to a treatment of reducing friction between the intubation tube and the inner surface of the recess.

9. The intubation assistance instrument as claimed in claim 1, wherein the tube restriction portion prevents the intubation tube inserted into the recess from being removed from the recess in a direction towards an opening side of the recess.

10. The intubation assistance instrument as claimed in claim 1, wherein the assistance instrument main body has a plate-like protruding portion provided on a distal end portion of the assistance instrument main body so as to protrude in a frontward direction.

11. The intubation assistance instrument as claimed in claim 10, wherein the assistance instrument main body includes a curved portion formed at a roughly middle part thereof, the curved portion having a curved inner side, and wherein the protruding portion is formed so as to continuously extend from the curved inner side at the distal end portion of the assistance instrument main body.

12. An intubation assistance apparatus, comprising:
the intubation assistance instrument defined by claim 1;
an apparatus main body to which the assistance instrument main body of the intubation assistance instrument is mounted; and
an image light acquirer that acquires image light of an observation site at which a distal end portion of the intubation assistance instrument is positioned.

13. The intubation assistance apparatus as claimed in claim 12, wherein the guide member can be attached on and detached from the first side portion of the assistance instrument main body in a state that the assistance instrument main body is mounted to the apparatus main body.

14. An intubation assistance system, comprising:
the intubation assistance apparatus defined by claim 12; and
an insertion tube to be inserted into the guide portion of the guide member of the intubation assistance instrument.

15. The intubation assistance instrument as claimed in claim 1, wherein the opened channel has an elongated aperture defined by an opening edge of the tube restriction portion of the assistance instrument main body and an opening edge of the inner wall of the recess, and wherein the opened channel has a cross-section of a circular arc shape in the direction perpendicular to the extending direction of the opened channel.

16. The intubation assistance instrument as claimed in claim 15, wherein the opened channel is configured to hold the intubation tube in a manner such that the intubation tube is removable from the guide portion, in the direction perpendicular to the extending direction of the opened channel and away from the first side portion of the assistance instrument main body, through the elongated aperture of the opened channel.

17. The intubation assistance instrument as claimed in claim 1, wherein the rib is formed so as to extend from the first side portion of the assistance instrument main body in a width direction of the assistance instrument main body.

18. The intubation assistance instrument as claimed in claim 16, wherein the elongated aperture of the opened channel extends along an entire length of the tube restriction portion of the assistance instrument main body in the longitudinal direction of the guide member.

19. The intubation assistance instrument as claimed in claim 1, wherein the tube restriction portion is integrally formed with the assistance instrument main body.

20. The intubation assistance instrument as claimed in claim 1, wherein the opened channel has a proximal end portion for introducing the intubation tube into the opened channel and a distal end from which the intubation tube introduced into the opened channel protrudes, and wherein the opened channel is configured to hold the intubation tube in a manner such that the intubation tube is removable from the guide portion in the direction perpendicular to the extending direction of the opened channel and away from the first side portion of the assistance instrument main body when the intubation tube is introduced from the proximal end of the opened channel and protrudes from the distal end of the opened channel.

* * * * *